(12) United States Patent
Ashraf et al.

(10) Patent No.: US 9,744,085 B2
(45) Date of Patent: *Aug. 29, 2017

(54) WEARABLE ARTICLE WITH OUTWARDMOST LAYER OF MULTICOMPONENT FIBER NONWOVEN PROVIDING ENHANCED MECHANICAL FEATURES

(71) Applicant: The Procter & Gamble Company, Cincinnati, OH (US)

(72) Inventors: Arman Ashraf, Mason, OH (US); Shrish Yashwant Rane, Madeira, OH (US); Mark James Kline, Okeana, OH (US); Fang Liu, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 218 days.

This patent is subject to a terminal disclaimer.

(21) Appl. No.: 14/682,160

(22) Filed: Apr. 9, 2015

(65) Prior Publication Data

US 2015/0209201 A1    Jul. 30, 2015

Related U.S. Application Data

(63) Continuation of application No. 13/538,177, filed on Jun. 29, 2012, now Pat. No. 9,056,032.

(51) Int. Cl.
*A61F 13/62* (2006.01)
*A61F 13/514* (2006.01)

(52) U.S. Cl.
CPC ............ *A61F 13/62* (2013.01); *A61F 13/514* (2013.01); *A61F 13/5148* (2013.01);
(Continued)

(58) Field of Classification Search
CPC ...... A61F 13/62; A61F 13/622; A61F 13/625; A61F 13/627; A44B 18/0011; A44B 18/0034; A44B 18/0057
See application file for complete search history.

(56) References Cited

U.S. PATENT DOCUMENTS 3,138,841 A    6/1964 Naimer
3,192,589 A    7/1965 Pearson
(Continued)

FOREIGN PATENT DOCUMENTS

EP    0 381 087 A1    8/1990
EP    1 290 960 A1    12/2003
(Continued)

OTHER PUBLICATIONS

All Office Actions, U.S. Appl. No. 13/538,140.
All Office Actions, U.S. Appl. No. 13/538,178.
PCT International Search Report, dated Aug. 20, 2013 (9 pages).

*Primary Examiner* — Lynne Anderson
(74) *Attorney, Agent, or Firm* — Christian M. Best; William E. Gallagher

(57) ABSTRACT

A fastening system comprising a nonwoven web material operable to fastenably engage a fastening component is disclosed. The nonwoven web material may comprising multicomponent fibers having a polyolefin component and a polyamide component, and a machine direction bias. The nonwoven web material may bear an impressed pattern of thermal bonds having an average frequency along any line that can be identified in the machine direction, of at least 0.5 bonds per cm.

20 Claims, 19 Drawing Sheets

(52) U.S. Cl.
CPC ...... *A61F 13/51478* (2013.01); *A61F 13/622* (2013.01); *A61F 13/627* (2013.01)

(56) References Cited

U.S. PATENT DOCUMENTS

| | | |
|---|---|---|
| 3,266,113 A | 8/1966 | Flanagan |
| 3,408,705 A | 11/1968 | Kayser et al. |
| 3,557,413 A | 1/1971 | Engle |
| 3,594,863 A | 7/1971 | Erb |
| 3,594,865 A | 7/1971 | Erb |
| 3,608,024 A | 9/1971 | Yazawa et al. |
| 3,718,725 A | 2/1973 | Hamano |
| 3,762,000 A | 10/1973 | Menzin et al. |
| 3,860,003 A | 1/1975 | Buell |
| 4,001,366 A | 1/1977 | Brumlik |
| 4,056,593 A | 11/1977 | deNavas Albareda |
| 4,189,809 A | 2/1980 | Sotos |
| 4,290,174 A | 9/1981 | Kalleberg |
| 4,454,183 A | 6/1984 | Wollman |
| 4,515,595 A | 5/1985 | Kievit et al. |
| 4,695,278 A | 9/1987 | Lawson |
| 4,707,893 A | 11/1987 | Hashizume et al. |
| 4,783,231 A | 11/1988 | Raley |
| 4,846,815 A | 7/1989 | Scripps |
| 4,894,060 A | 1/1990 | Nestegard |
| 4,909,803 A | 3/1990 | Aziz et al. |
| 5,077,870 A | 1/1992 | Melbye et al. |
| 5,108,820 A | 4/1992 | Kaneko |
| 5,151,092 A | 9/1992 | Buell et al. |
| 5,221,274 A | 6/1993 | Buell et al. |
| 5,256,231 A | 10/1993 | Gorman et al. |
| 5,315,740 A | 5/1994 | Provost |
| 5,318,555 A | 6/1994 | Siebers et al. |
| 5,326,612 A | 7/1994 | Goulait |
| 5,407,439 A | 4/1995 | Goulait |
| 5,436,051 A | 7/1995 | Donaruma et al. |
| 5,595,567 A | 1/1997 | King et al. |
| 5,605,739 A | 2/1997 | Stokes et al. |
| 5,607,635 A | 3/1997 | Melbye et al. |
| 5,669,900 A | 9/1997 | Bullwinkel et al. |
| 5,679,302 A | 10/1997 | Miller et al. |
| 5,733,822 A | 3/1998 | Gessner et al. |
| 5,759,926 A | 6/1998 | Pike et al. |
| 5,773,120 A | 6/1998 | Deka et al. |
| 5,811,045 A | 9/1998 | Pike |
| 5,845,375 A | 12/1998 | Miller et al. |
| 5,855,784 A | 1/1999 | Pike et al. |
| 5,858,515 A | 1/1999 | Stokes et al. |
| 5,879,604 A | 3/1999 | Melbye et al. |
| 5,895,710 A | 4/1999 | Sasse et al. |
| 5,964,742 A | 10/1999 | Mccormack et al. |
| 6,054,091 A | 4/2000 | Miller et al. |
| 6,169,045 B1 | 1/2001 | Pike et al. |
| 6,200,669 B1 | 3/2001 | Marmon et al. |
| 6,206,679 B1 | 3/2001 | Provost et al. |
| 6,209,177 B1 | 4/2001 | Murasaki |
| 6,218,593 B1 | 4/2001 | Torimae |
| 6,248,419 B1 | 6/2001 | Kennedy et al. |
| 6,296,629 B1 | 10/2001 | Siebers et al. |
| 6,352,948 B1 | 3/2002 | Pike et al. |
| 6,357,088 B2 | 3/2002 | Provost et al. |
| 6,481,063 B2 | 11/2002 | Shepard et al. |
| 6,589,638 B1 | 7/2003 | McCormack et al. |
| 6,617,023 B2 | 9/2003 | Tsutsui et al. |
| 6,637,079 B1 | 10/2003 | Goulait |
| 6,686,303 B1 | 2/2004 | Haynes et al. |
| 6,715,189 B2 | 4/2004 | Osbon et al. |
| 6,720,278 B2 | 4/2004 | Wenstrup |
| 6,723,669 B1 | 4/2004 | Clark et al. |
| 6,737,114 B2 | 5/2004 | Dawson et al. |
| 6,739,023 B2 | 5/2004 | Vonfeldt et al. |
| 6,770,065 B1 | 8/2004 | Sasaki et al. |
| 6,777,056 B1 | 8/2004 | Boggs et al. |
| RE38,652 E | 11/2004 | Provost |
| 6,838,402 B2 | 1/2005 | Harris et al. |
| 6,863,697 B2 | 3/2005 | McDaniel et al. |
| 6,878,650 B2 | 4/2005 | Clark et al. |
| 6,982,055 B2 | 1/2006 | Seth et al. |
| 7,014,906 B2 | 3/2006 | Tuman et al. |
| 7,032,278 B2 | 4/2006 | Kurtz |
| 7,048,818 B2 | 5/2006 | Krantz et al. |
| 7,052,636 B2 | 5/2006 | Ausen et al. |
| 7,052,638 B2 | 5/2006 | Clarner et al. |
| 7,067,185 B2 | 6/2006 | Ausen et al. |
| 7,172,008 B2 | 2/2007 | Vanbenschoten et al. |
| 7,182,992 B2 | 2/2007 | Ausen et al. |
| 7,185,401 B2 | 3/2007 | Ausen et al. |
| 7,188,396 B2 | 3/2007 | Melbye et al. |
| 7,189,220 B2 | 3/2007 | Miyoshi et al. |
| 7,325,421 B2 * | 2/2008 | Sasser ................ A44B 18/0034 66/195 |
| 7,326,663 B2 | 2/2008 | Sodemann et al. |
| 7,516,524 B2 | 4/2009 | Provost et al. |
| 7,547,469 B2 * | 6/2009 | Provost .............. A44B 18/0011 428/88 |
| 7,789,870 B2 | 9/2010 | Horn et al. |
| 7,855,316 B2 | 12/2010 | Meyer et al. |
| 7,870,652 B2 | 1/2011 | Kline et al. |
| 7,883,772 B2 | 2/2011 | Pourdehimi et al. |
| 7,895,718 B2 | 3/2011 | Horn et al. |
| D640,064 S | 6/2011 | Horn et al. |
| 7,981,822 B2 | 7/2011 | Lester et al. |
| 8,016,807 B2 | 9/2011 | Kline et al. |
| 8,034,430 B2 | 10/2011 | Efremova et al. |
| 8,052,666 B2 | 11/2011 | Sawyer et al. |
| 8,449,518 B2 | 5/2013 | Allison-Rogers |
| 8,722,963 B2 | 5/2014 | Kanya et al. |
| 9,056,032 B2 * | 6/2015 | Ashraf ................ A61F 13/514 |
| 9,084,701 B2 * | 7/2015 | RamosMedina .... A61F 13/5633 |
| 2001/0037850 A1 | 11/2001 | Marmon et al. |
| 2003/0077430 A1 | 4/2003 | Grimm et al. |
| 2003/0162459 A1 | 8/2003 | Osbon et al. |
| 2003/0176132 A1 | 9/2003 | Moriyasu et al. |
| 2003/0199220 A1 | 10/2003 | Dawson et al. |
| 2004/0121121 A1 | 6/2004 | Anderson et al. |
| 2005/0048281 A1 | 3/2005 | Royer et al. |
| 2005/0191460 A1 | 9/2005 | Belau |
| 2005/0202205 A1 | 9/2005 | Peterson et al. |
| 2006/0234049 A1 | 10/2006 | Van Dun |
| 2007/0143972 A1 | 6/2007 | Kline et al. |
| 2007/0178795 A1 | 8/2007 | Stralin et al. |
| 2007/0275622 A1 | 11/2007 | Masuda et al. |
| 2009/0042475 A1 | 2/2009 | Pourdehimi |
| 2009/0137975 A1 | 5/2009 | Kohira et al. |
| 2010/0062231 A1 | 3/2010 | Abed et al. |
| 2010/0280481 A1 | 11/2010 | Kline et al. |
| 2011/0056053 A1 | 3/2011 | Kline et al. |
| 2011/0092947 A1 | 4/2011 | Kline et al. |
| 2011/0197404 A1 | 8/2011 | Terada et al. |
| 2012/0133194 A1 | 5/2012 | Takehara et al. |
| 2013/0023177 A1 | 1/2013 | Classen et al. |
| 2013/0138073 A1 | 5/2013 | Horn et al. |
| 2014/0047678 A1 | 2/2014 | Horn et al. |
| 2014/0066872 A1 | 3/2014 | Baer et al. |
| 2014/0228799 A1 | 8/2014 | Kline et al. |

FOREIGN PATENT DOCUMENTS

| | | |
|---|---|---|
| WO | WO 96-04812 A1 | 2/1996 |
| WO | WO 96-22065 A1 | 7/1996 |
| WO | WO 2007-096842 A1 | 8/2007 |
| WO | WO 2007-097467 A1 | 8/2007 |
| WO | WO 2010-135508 A1 | 11/2010 |

* cited by examiner

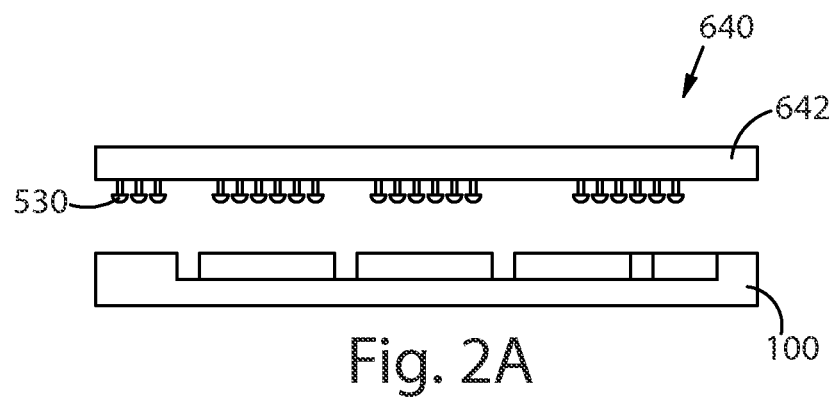

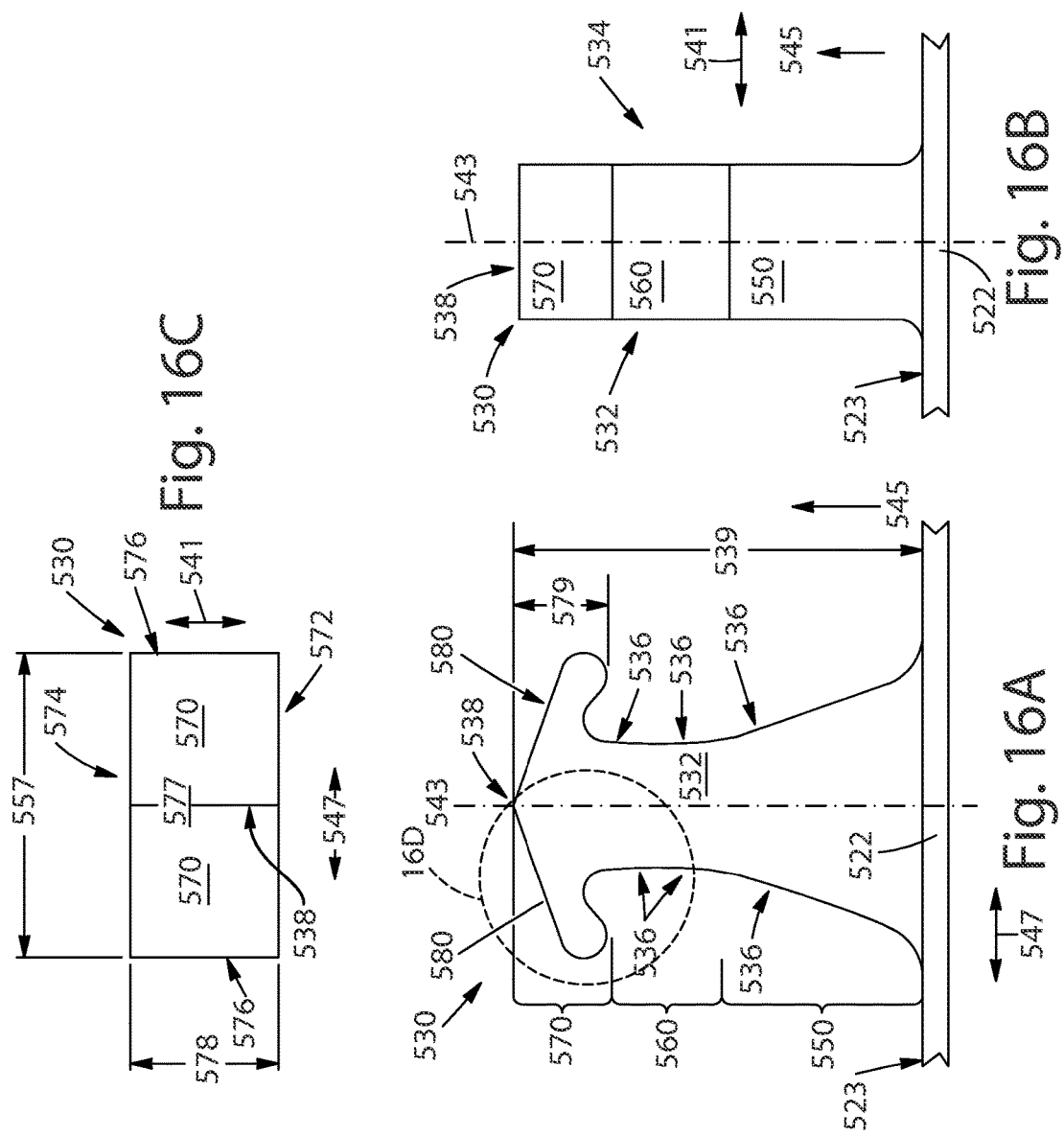

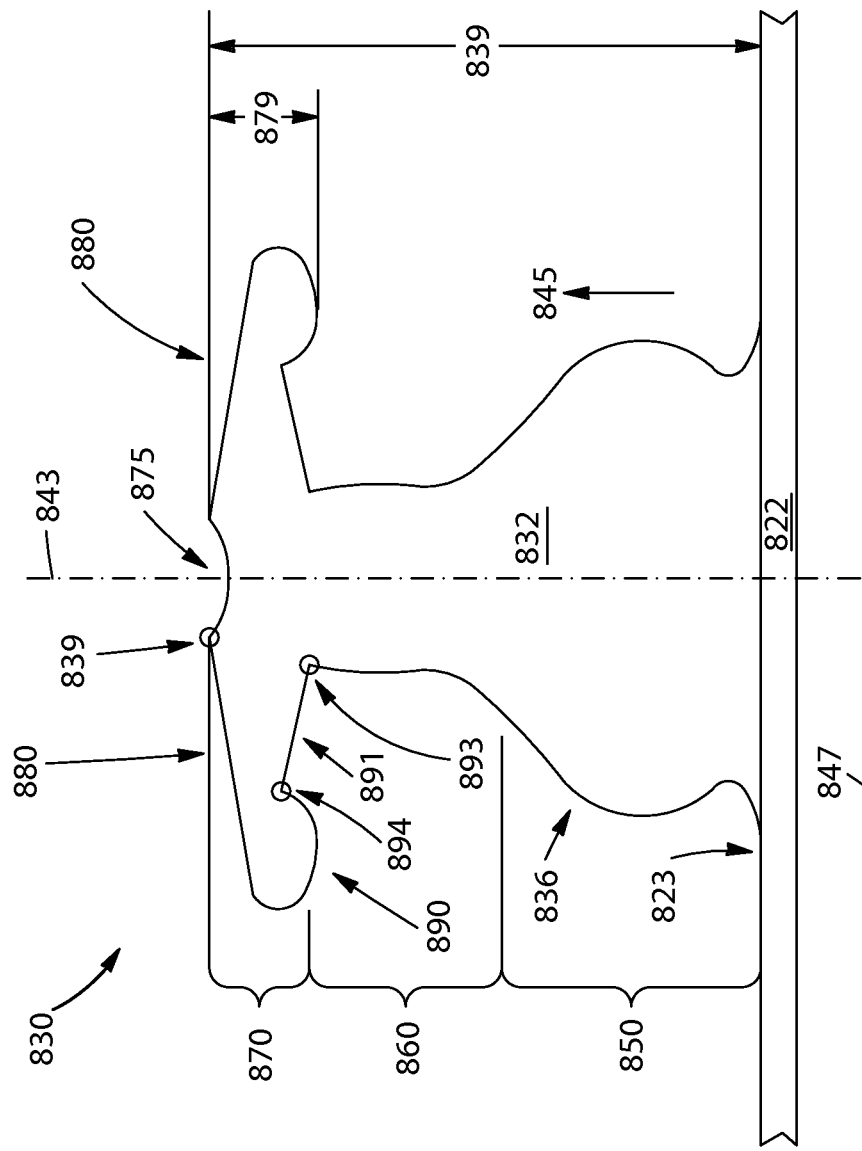

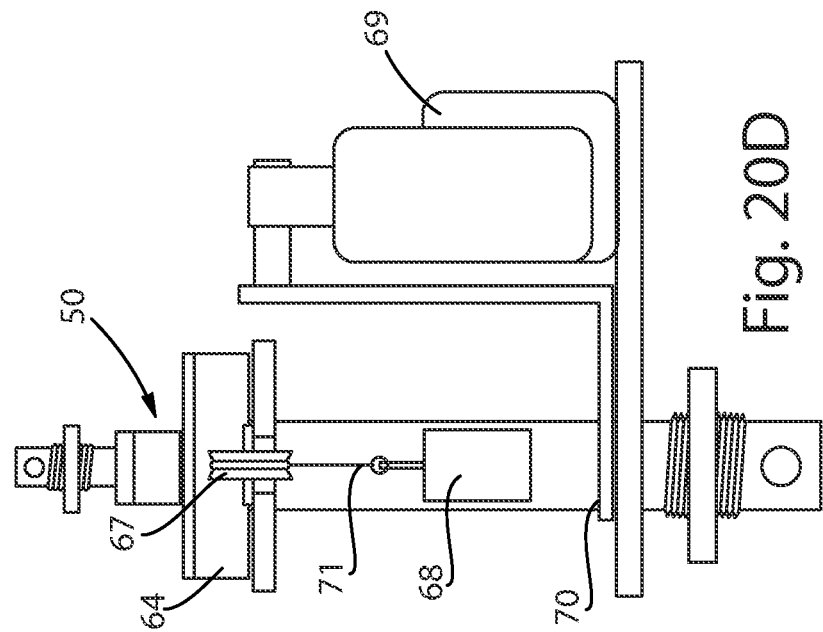
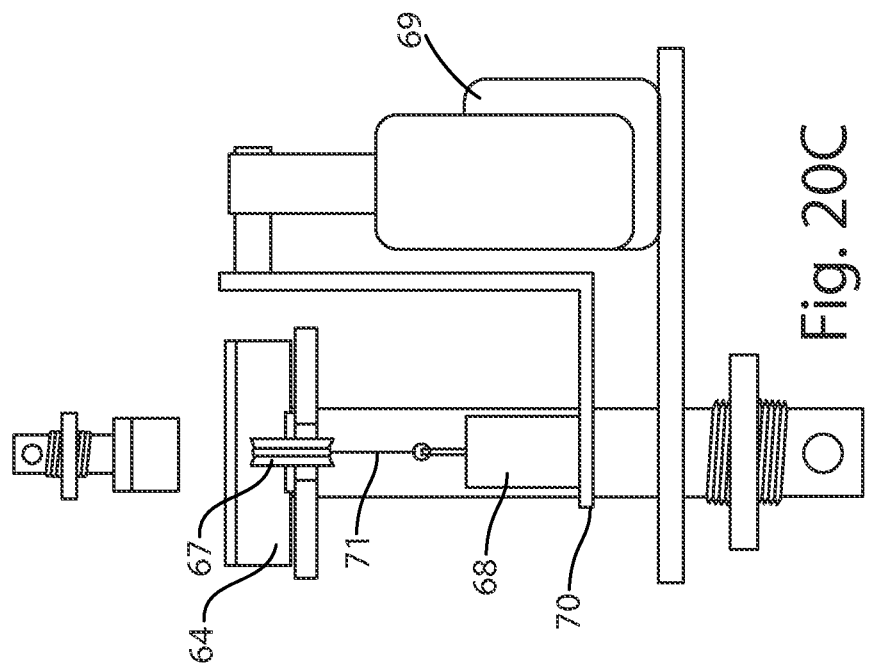

WEARABLE ARTICLE WITH OUTWARDMOST LAYER OF MULTICOMPONENT FIBER NONWOVEN PROVIDING ENHANCED MECHANICAL FEATURES

CROSS REFERENCE TO RELATED APPLICATION

This application is a continuation of U.S. Nonprovisional application Ser. No. 13/538,177, filed Jun. 29, 2012, the entirety of which are incorporated by reference herein.

BACKGROUND OF THE INVENTION

Many wearable articles are designed to be fastened about a wearer via a hook-and-loop fastening system. A hook-and-loop fastening system is exemplified by the VELCRO system; it includes a hooks component, which is a patch of usually plastic material having a dense pattern of small flexible upstanding hook structures, T-shaped structures, arrow-shaped structures, mushroom-shaped structures or other structures formed thereon; and a loops component, which is a patch or section of substrate material having a dense disposition of upstanding fiber loops or other sections of fibers connected to the substrate in such as way as to extend away from the substrate while having ends attached to the substrate. When the hooks component is brought into contact with the loops component under pressure (usually applied by the fingers), the individual hook structures engage loops structures and catch therein. Substantial attachment strength, especially resistive to separation in a shearing mode, may be obtained by the cumulative effect of many hooks on the hooks patch engaging many loops on the loops component. Since their introduction, hook-and-loop fastening systems have been refined and specialized in design for varying applications, and have proven popular and effective. They provide a quick and convenient mechanism for fastening one member to another member in a way that can conveniently and effectively substitute for older types of fastening or attachment systems such as buttons, snaps, ties, zippers, etc. Additionally, various hooks designs have been created for engaging various types of loops components. In some cases hooks designs are suitable for engaging and hooking into the fibers of various types of fabrics without the necessity of a specially provided loops component.

Currently, many disposable diapers include hook-and-loop fastening systems. A typical disposable diaper may include a central chassis having front and rear regions, and a pair of fastening members or ears extending laterally from the rear region. Each of the fastening members may have disposed thereon a patch of hooks. The outside of the front region may have disposed thereon a corresponding patch of loops material, often called the "landing zone." The diaper may be applied to a wearer by positioning the rear region of the diaper beneath the wearer while in a reclining position, wrapping the front region of the diaper between the wearer's legs and up over the front of the wearer's lower torso, wrapping each of the fastening members about a hip, and attaching each fastening member via the hooks patch to the landing zone, thereby forming a pant-like structure about the wearer. Various types of specialized hook and loops materials have been developed specifically for use on disposable diapers.

More recently, it has been found that a nonwoven material having suitable characteristics and features, may serve as a suitable loops material; see, for example, U.S. Pat. No. 7,789,870. The cited patent discloses a nonwoven formed of bicomponent fibers. The bicomponent fibers have longitudinal components formed of differing polyolefins. The bicomponent fibers are formed by ejecting or extruding the differing polyolefins in a molten state under pressure, from specially adapted spinnerets situated in banks along a nonwoven web forming line. The spinnerets separately form the longitudinal components and then urge them together while the polymers are still molten, thereby forming bicomponent fibers having two distinct longitudinal components. When the longitudinal components are appropriately configured with respect to one another within the fiber, as a result of differing properties of the differing polyolefins including differing rates and/or extents of contraction upon cooling, after exiting the spinnerets the bicomponent fibers curl or "crimp" as they cool. When such crimped fibers are subsequently laid down to form a nonwoven batt and then consolidated and bonded in an appropriate pattern, they form attached loop-like structures that may make the resulting nonwoven web suitable for use as a loops material in some applications, including disposable diapers.

By competitive necessity, the business of manufacturing disposable diapers is a relatively capital-intensive, high-volume, low margin-per-article business. Consequently, any improvement in the product or its manufacture that can save even to a small extent on costs of materials or manufacture without sacrificing performance, or any improvement that enhances performance without increasing cost, can provide significant competitive advantages to the manufacturer. Improvements to nonwoven materials used to form loops components of landing zones, and improvements in fastening systems including such nonwovens, are no exception. While current technologies including the above-cited '870 patent have provided a nonwoven web material that serves satisfactorily as loops material in certain applications, further improvements in the fastening/holding capabilities and/or reductions in cost would be advantageous in these applications and others.

BRIEF DESCRIPTION OF THE DRAWINGS

FIG. 2A is an elevation view showing an example of a fastening system;

FIG. 16A is an enlarged view of a front of an example of a bidirectional micro-sized hook disposed on a surface of a substrate of a hooks patch material;

FIG. 16B is an enlarged side view of the hook of FIG. 16A;

FIG. 16C is an enlarged top view of the hook of FIG. 16A;

FIG. 17 is an enlarged view of a front of another example of a bidirectional micro-sized hook disposed on a surface of a substrate of a hooks patch material;

FIG. 20C is a schematic end view of certain components of a fixture used to perform the Separation Resistance test described herein, in a first position; and FIG. 20D is a schematic end view of certain components of a fixture used to perform the Separation Resistance test described herein, in a second position.

DETAILED DESCRIPTION OF EXAMPLES

Definitions

Figure 1A:
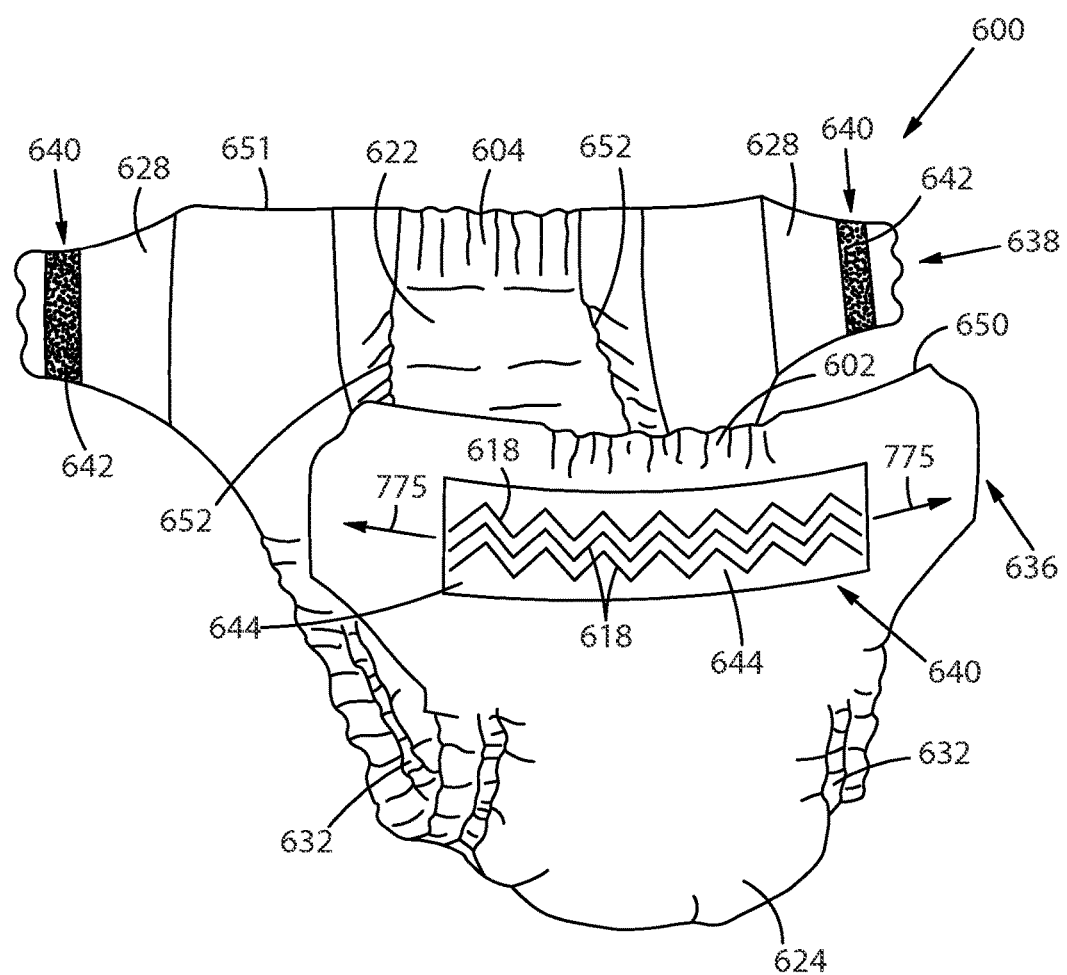
FIG. 1A is a perspective view of a disposable absorbent article.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments and pads, feminine hygiene products, breast pads, care mats, bibs, wound dressing products, and the like. As used herein, the term "exudates" includes, but is not limited to, urine, blood, vaginal discharges, breast milk, sweat and fecal matter.

"Bicomponent fiber" refers to a fiber having a cross-section comprising two discrete polymer components, two discrete blends of polymer components, or one discrete polymer component and one discrete blend of polymer components. A bicomponent fiber is encompassed within the term "multicomponent fiber." A bicomponent fiber may have an overall cross section divided into two or more subsections of the differing components of any shape or arrangement, including, for example, coaxial subsections, core-and-sheath subsections, side-by-side subsections, radial subsections, etc.

"Cross direction"—with respect to a web material, refers to the direction along the web material substantially perpendicular to the direction of forward travel of the web material through the manufacturing line in which the web material is manufactured.

"Cross direction bias," with respect to a bond shape forming a component of a bond pattern impressed on a nonwoven web, means that the bond shape, as situated on the web, has a length with a machine direction vector component that is less than its cross direction vector component.

"Multicomponent fiber" refers to a fiber having a cross-section comprising more than one discrete polymer component, more than one discrete blend of polymer components, or at least one discrete polymer component and at least one discrete blend of polymer components. The term "multicomponent fiber" encompasses, but is not limited to, a bicomponent fiber. A multicomponent fiber may have an overall cross section divided into subsections of the differing components of any shape or arrangement, including, for example, coaxial subsections, core-and-sheath subsections, side-by-side subsections, radial subsections, etc.

"Machine direction"—with respect to a web material, refers to the direction along the web material substantially parallel to the direction of forward travel of the web material through the manufacturing line in which the web material is manufactured.

"Machine direction bias", with respect to the fibers forming a nonwoven web, means that a majority of the fibers, as situated in the web with the web unstretched, have lengths with machine direction vector components that are greater than their cross direction vector components.

A "nonwoven" is a manufactured sheet or web of directionally or randomly oriented fibers, consolidated and bonded together by friction, cohesion, adhesion or one or more patterns of bonds and bond impressions created through localized compression and/or application of heat or heating energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven webs may be formed by many processes such as meltblowing, spunbonding, solvent spinning, electrospinning, and carding. The basis weight of nonwoven webs is usually expressed in grams per square meter (gsm).

"Separation Resistance" refers to the capacity of a fastening system including a patch of hooks material and a patch of loops material to resist forcible separation after having been brought into engagement by application of a given pressure and subjected to a given shear force, as determined through application of the Separation Resistance test method described herein.

"Thermal bond" refers to a bond joining polymeric fibers, or joining polymeric fibers and other polymeric structures, wherein the structures have been deformed and at least partially fused or welded together by application of pressure and heating energy. "Thermal bonding" refers to the process for creating thermal bonds, which may, for example, involve use of a pair of rollers configured to form a nip, wherein at least one of the rollers has a bonding pattern of raised surfaces and depressions machined, etched, or otherwise formed on its outer cylindrical surface so as to impress a bond pattern reflecting the raised surfaces, on a web passing through the nip. One or both rollers may have heating energy supplied thereto, or heating energy may be supplied proximate the nip, so as to heat the materials of the web as they pass through the nip and cause them to melt to some extent. Heating energy supplied may be in the form of heat (conveyed in, e.g., heated oil circulated through a bonding roller), or may have other forms, such as, e.g., ultrasonic energy, which when applied have the effect of generating heat energy within the materials of the web to cause melting.

Figure 1B:
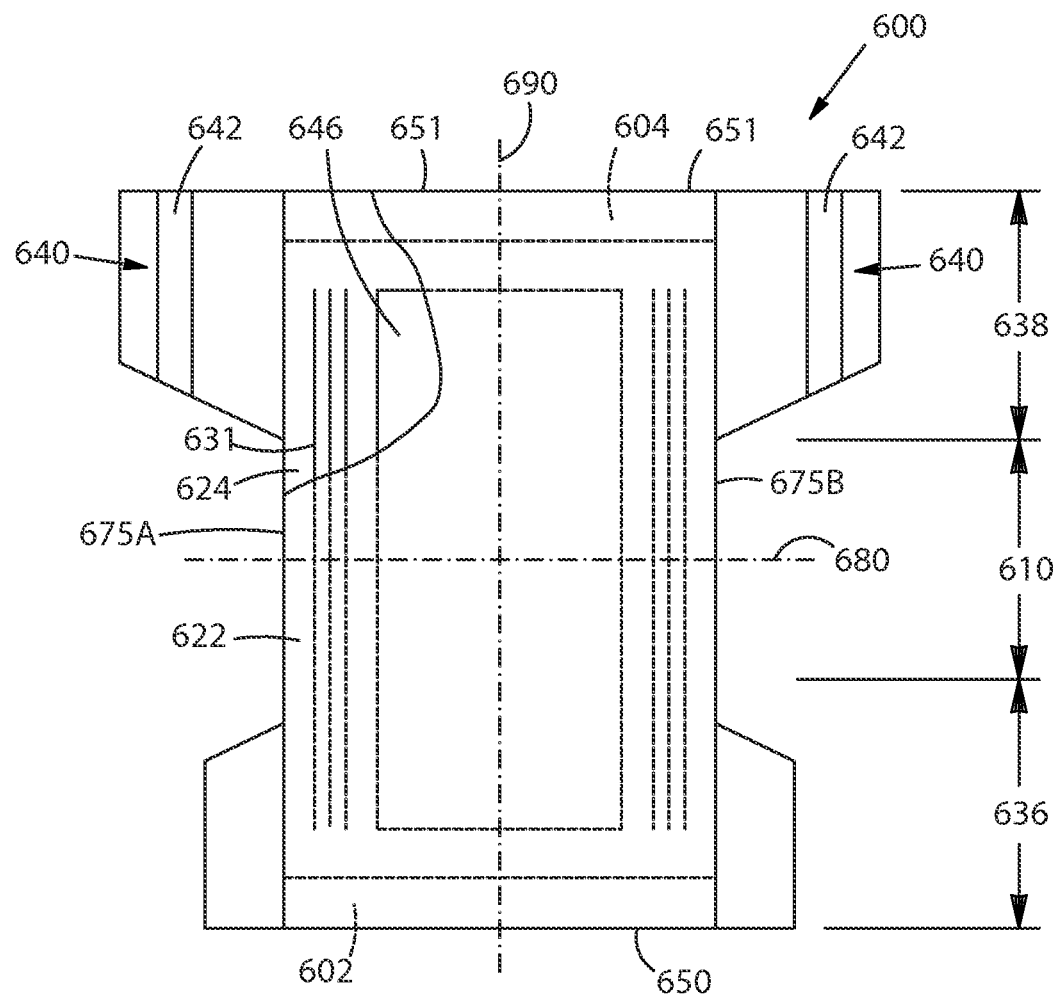
FIG. 1B is a plan view of the disposable absorbent article of FIG. 1A in a flattened-out uncontracted state.

FIGS. 1A and 1B depict an example of a wearable disposable absorbent article 600 in the form of a disposable diaper. It may include a central chassis having a liquid permeable topsheet 622, a liquid impermeable backsheet 624, and an absorbent core 646 disposed between the topsheet and the backsheet. A pair of fastening members 628 may extend laterally from the chassis in the rear region. Fastening members 628 may be laterally extensible and also elastically extensible, and be formed of an elastically extensible stretch laminate material such as disclosed in, for example, U.S. Pat. No. 7,870,652, and U.S. application Ser. Nos. 11/638,988; 12/773,181; and 12/904,220 by Kline et al. Fastening members 628 may have disposed thereon hooks patches 642. The outside surface of the front region may have disposed thereon a landing zone 644 which is formed at least in part of a material adapted to serve as a loops material suitable for fastenable engagement with hooks patches 642.

Article 600 may be applied to a wearer in the manner described in the Background. If fastening members 628 are laterally elastically extensible, the diaper may be imparted with a comfortable and snug elastic fit about the wearer's waist.

Landing zone 644 may be formed at least in part of a suitably adapted nonwoven web material, such as described in U.S. Pat. No. 7,789,870. The '870 patent describes a landing zone with an outer layer of a nonwoven web material, formed of composite fibers (herein, "bicomponent" or "multicomponent" fibers).

General

Figure 13A:
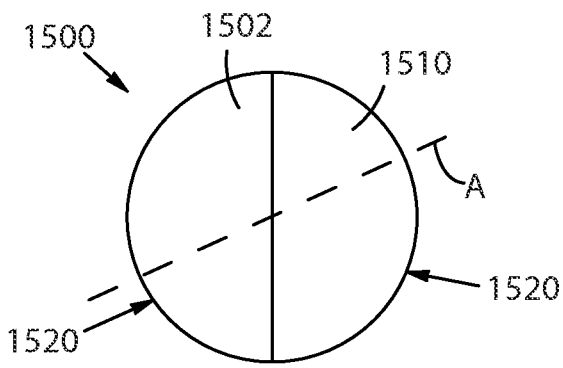
FIGS. 13A-13D are schematic cross sectional views of bi-component fibers in various configurations.

The landing zone 644 may comprise a section of nonwoven web. A nonwoven web that may be suitable for use as a component of a landing zone as contemplated herein may comprise a nonwoven web made of a crimped composite fiber (hereinafter referred to as multicomponent fiber). The crimped multicomponent fiber may comprise a first section of a first polymer and a second section of a second polymer. The first and second sections may be arranged to occupy substantially separate areas of the cross sections of the multicomponent fibers and extend continuously along the fiber length. In some examples, each of the first and second sections forms at least a part of the outer surface along the length of the multicomponent fiber. In some examples, as shown in FIG. 13A, a multicomponent fiber 1500 may be a side-by-side type multicomponent fiber where a first polymer section 1502 and a second polymer section 1510 extend side-by-side along the length of the multicomponent fiber such that the first and the second polymer sections 1502 and 1510 each form about 50% of the outer surface 1520 of the multicomponent fiber 1500.

Arrangement of Fiber Components; Fiber Components Characteristics; Crimping

Figure 13B:
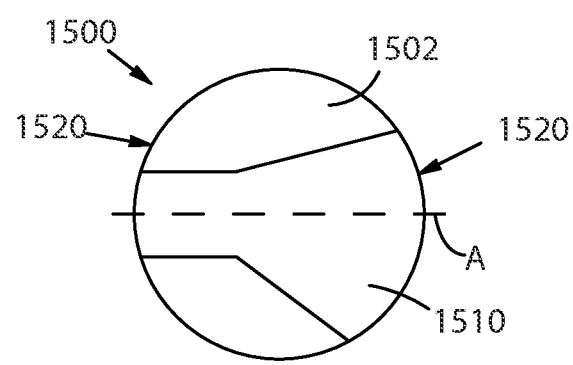
Figure 13C:
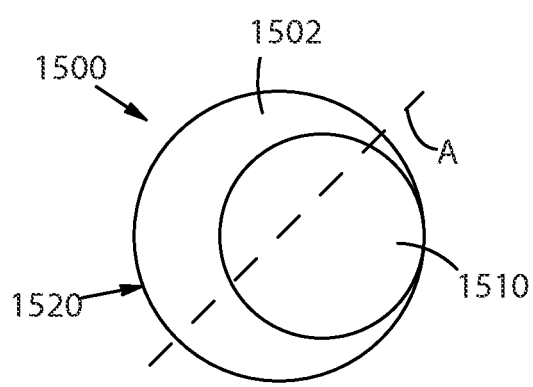
Figure 13D:
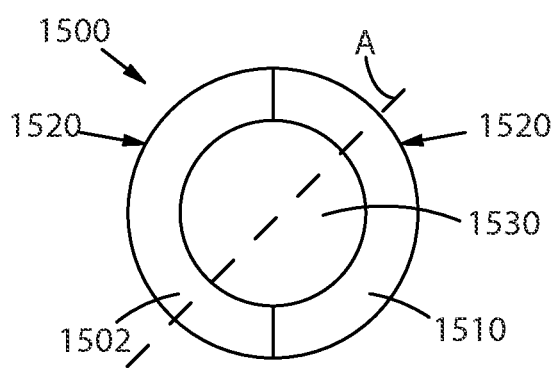

The first polymer section 1502 and the second polymer section 1510 may be arranged in any suitable configuration which would effect crimping in the fiber 1500 following spinning. In some examples, such as shown in FIG. 13B, the second polymer section 1510 may form a cross like pattern within the first polymer section 1502, which is asymmetrically distributed within the first polymer section. In some examples, such as shown in FIG. 13C, the second polymer section 1510 may be completely surrounded by the first polymer section 1502 in, e.g., a sheath-core arrangement, such that the first polymer section 1502 comprises about 100% of the outer surface 1520 of the multicomponent fiber 1500. The second polymer section 1510 may be disposed within the first polymer section 1502 asymmetrically or eccentrically such that a crimp results in the resulting fiber 1500. Expressed in an alternative fashion, it may be desirable that, when a cross section is taken through a fiber 1500 as suggested in FIGS. 13A-D, there exists an axis lying in the plane of the cross section that equally divides the total area of the cross section, across which the area occupied by at least one of the first polymer section 1502 and second polymer section 1510 is unequally distributed. The examples of cross sections depicted in FIGS. 13A-D satisfy such condition; the area occupied by at least one of first polymer section 1502 and second polymer section 1510 is unequally distributed about axis A in each of the figures. Without intending to be bound by theory, it is believed that the examples of FIGS. 13A (first and second polymer components in a side-by-side arrangement and 13C (first and second polymer components in an eccentric sheath-core arrangement) are best suited to facilitate spinning and provide optimal crimping of the fibers. In an alternative example, as shown in FIG. 13D, the first polymer section 1502 and the second polymer section 1510 may be in a side-by side orientation defining an opening or cavity 1530 between the first polymer section 1502 and the second polymer section 1510. In another example, the opening or cavity 1530 may be occupied by one or more additional polymer components. Generally, however, any arrangement in which the fibers crimp upon exiting spinnerets and cooling, is contemplated.

Weight Ratio

Where the first polymer is polyolefin and second polymer is non-polyolefin as described below, and the non-polyolefin has either or both of greater tensile strength or greater stiffness than the polyolefin, the weight ratio of the first polymer to the second polymer in multicomponent fibers forming a multicomponent fiber nonwoven web may be, in some examples, in the range of about 10:90 to about 90:10. It may be more preferred, however that the weight ratio of the first polymer to the second polymer in multicomponent fibers forming a multicomponent fiber nonwoven web may be in the range of about 50:50 to 90:10, or 60:40 to 80:20, and even more preferred that the ratio be in the range of about 65:35 to 75:25. These ranges may be desired to strike a balance between usage of the polymer with the greater strength (which may help impart separation resistance as described herein), and cost effectiveness, where the greater-strength material is the more expensive. Further, to attain the separation resistance contemplated for uses described herein the basis weight of the second polymer in the nonwoven substrate may be greater than 1 gsm.

Moreover, where the first polymer is polypropylene and the second polymer is polyamide, as described below, generally the polyamide component of the fiber will have the greater tensile strength. For this reason, it might be deemed intuitive that merely increasing the weight ratio of the polyamide component to the polyolefin component will automatically increase the fiber strength of the multicomponent fiber nonwoven, and thus, of the separation resistance of a hook-and-loop fastening system in which the multicomponent fiber nonwoven forms the loops component—the only constraint being the cost of the polyamide. However, it is believed that this is not the case. Rather, it is believed that increasing the ratio of the polyamide to the polyolefin beyond a certain point may adversely affect the separation resistance performance of a hook-and-loop fastening system in which the multicomponent nonwoven web forms the loops component.

Without intending to be bound by theory, it is believed that the weight ratio of a polyamide component to a polyolefin component in a two-component multicomponent fiber nonwoven web, as described herein, affects several important features of the multicomponent fibers, and thus, of the thermally bonded nonwoven web formed of the fibers. These include but are not limited to the extent and frequency of fiber crimp; the extent to which inter-fiber thermal bonds may be formed without the need for excessive heating (which may excessively melt or even degrade the polyolefin component, causing processing complications and product deficiencies); the strength of the bonds; and the extent to which the fiber components will remain adhered or bonded together along the free lengths of the multicomponent fibers following spinning, bonding, downstream processing, and in subsequent use. Thus, it is believed that a multicomponent fiber nonwoven, with polyolefin and polyamide fiber components, will serve as a loops component of a hook-and-loop fastening system exhibiting the best separation resistance performance when the weight ratio of polyolefin to polyamide is from about 50:50 to about 90:10, more preferably from 60:40 to 80:20, and more preferably from 65:35 to 75:25.

It may be desirable in some circumstances to include more than two polymer components in the multicomponent fibers. In that event, assuming that one component is still polyamide, it remains preferable that the weight ratio of non-polyamide to polyamide be from about 50:50 to about 90:10, more preferably from 60:40 to 80:20, and more preferably from 65:35 to 75:25.

Fiber Components Characteristics

In some examples, the melting point of the first polymer forming first polymer section 1502 may be at least 40° C. lower than the melting point of the second polymer forming second polymer section 1510. In some examples the difference between the respective melting points of the first polymer forming first polymer section 1502 and the second polymer forming second polymer section 1510 may be 40° C. to 120° C.

In some examples, the melting point of the first polymer may be in a range of about 60° C. to about 300° C., more preferably 100° C. to 220° C., and even more preferably 120° C. to 180° C.

When the first polymer is, e.g., a polyolefin and the second polymer is a non-polyolefin such as a polyester or a polyamide, the first and second polymers may have substantially differing physical properties. Thus, in selecting the first and second polymers to form components of multicomponent fibers, it may be deemed desirable that the polymers are selected to have a compatibility such that they may be spun together under similar conditions (e.g., temperature and spinning pressure and/or rate) to enable them to be simultaneously ejected smoothly and uniformly from the spinnerets to form relatively uniform and consistent multi-component fibers whose cross sections do not vary substantially along their lengths. Thus, it may be desirable that the first polymer and the second polymer be selected to have properties such as melt viscosities at the operational spinning temperature(s) that do not differ substantially from one another. For example, it may be deemed desirable that the first and second polymers have respective melting points that differ within the ranges set forth above. Similarly, it may be deemed desirable that the first and second polymers selected have respective densities that are within 0.11 g/cm$^3$ to 0.45 g/cm$^3$ of each other.

Non-Polyamide Component; Polyolefin

When one of the first or second polymers is a non-polyamide component of the multicomponent fiber, propylene homopolymer and copolymers of propylene and one or more different types of α-olefins with 2-20 carbon atoms, preferably, 2-8 carbon atoms such as ethylene, 1-butene, 1-pentene, 1-hexene, 1-octene and 4-methyl-1-pentene, and having propylene as the primary structural unit may be utilized in some examples for one of the first or second polymers. Among those listed above, a propylene homopolymer or propylene-ethylene random copolymer having an ethylene unit content in the range of about 0 to about 10 mol % and melt flow rate (MFR) in the range of about 20 to about 200 g/10 min is desirable.

In some examples, the one of the first or second polymer may be a propylene homopolymer or a random copolymer of propylene and a small amount of ethylene having a uniform ethylene component content in the range of about 10 mol % or below, and preferably in the range of about 2 to about 10 mol %, from the standpoint of production of a nonwoven web having excellent fastening strength and mechanical strength as well as high bulkiness and softness that may be suitable for use as the loops component of a fastening system. In this case, the amount of ethylene unit component is obtained according to a standard method using $^{13}$C-NMR spectral analysis.

In some examples, the melting point of the one of the first or second polymer may be in the range of about 110 to about 180° C., or any individual number within the range. The aforementioned polymers may be produced utilizing a high stereospecific polymeric catalyst.

In a particularly preferred example, the first polymer may be a polypropylene (PP) having a density of about 0.9 g/cm$^3$ a melt flow rate of about 10 to about 100 g/10 min., or more preferably, about 20 g/10 min. to about 30 g/10 min. or even about 25 g/10 min; a molecular weight polydispersity from 2 to 4; and a melting point in the range of about 145° C. to 165° C.

Polyamide Component

In combination with the foregoing particularly preferred example or in another example, the second polymer may be a polyamide (PA) such as PA6, PA6-6, a copolymer of PA6 and PA6-6, PA6 and PA10 or PA6 and PA12. Most preferred may be PA6 (also known as nylon 6). The preferred density of the polyamide component may be about 1.11 to 1.15 g/cm$^3$. The preferred viscosity may be 120 cm$^3$/g to 230 cm$^3$/g. The preferred melting point may be 210° C. to 230° C.

Multi-Component Fiber with Non-Polyamide and Polyamide Components

In some examples, the first polymer may be a non-polyamide (such as a polyolefin) having the following properties:

Density: 0.7 g/cm$^3$ to 1.0 g/cm$^3$
Melt Flow Rate: 20.0 g/10 min to 100 g/10 min
Molecular Weight Polydispersity: 1.5-4.0 (Polystyrene narrow molecular weight distribution standard)
Melting Point: 110° C. to 180° C.

In these examples or in other examples, the second polymer may be a polyamide such as PA6, having the following properties:

Density: 1.11 g/cm$^3$ to 1.15 g/cm$^3$
Viscosity Number: 120 cm$^3$/g to 230 cm$^3$/g
Melting Point: 215° C. to 225° C.

Fiber Crimping

When a continuous multicomponent fiber is formed according to examples discussed above, the fiber may be imparted with crimps along its length. Crimps in fibers used to form a nonwoven web as described herein, combined with thermal bonding that binds the fibers to the web structure in a pattern that leaves portions of the lengths of the crimped fibers free to be engaged, may provide a bonded web that may be deemed suitable for use as a loops component of a hook-and-loop fastening system. It may be desirable that the number or frequency of crimps imparted to the fibers in the web be in the range of about 5 crimps to about 50 crimps/25 mm or any individual number within the range.

Additives

In addition to the polymers identified above, an appropriate amount of other components may be included in the multicomponent fiber. Some examples of suitable other components may include: heat stabilizers, weather resistance agents, a variety of stabilizers, antistatic agents, slip agents, anti-blocking agents, antifoggants, lubricants, dyes, pigments, natural oils, synthetic oils, waxes, etc. Some suitable examples of stabilizers include, antioxidants such as 2,6-di-t-butyl-4-methylphenol (BHT); phenolic antioxidants such as tetrakis[methylene-3-(3,5-di-t-butyl-4-hydroxyphenyl) propionate]methane, β-(3,5-di-t-butyl-4-hydroxyphenyl) alkyl ester propionate, and 2,2'-oxamidebis[ethyl-3-(3,5-di-t-butyl-4-hydroxyphenyl) propionate; fatty acid metal salts such as zinc stearate, calcium stearate, and calcium 1,2-hydroxystearate; polyhydric alcohol fatty acid esters such as glycidyl monostearate, glycidyl distearate, pentaerythritol monostearate, pentaerythritol distearate and pentaerythritol tristearate, etc. Furthermore, one or more different types of the components may be mixed and used in combination as well. Some examples of suitable lubricants include oleic acid amide, erucic acid amide, stearic acid amide, etc.

Furthermore, in some examples, the multicomponent fiber may further include fillers such as silica, diatomaceous earth, alumina, titanium oxide, magnesium oxide, pumice powder, pumice balloon, aluminum hydroxide, magnesium hydroxide, basic magnesium carbonate, dolomite, calcium sulfate, potassium titanate, barium sulfate, calcium sulfite, talc, clay, mica, asbestos, calcium silicate, montmorillonite, bentonite, graphite, aluminum powder, and molybdenum sulfide.

Mixing of polymer resin(s) and the optional components mentioned above may be achieved using any suitable conventional method.

Fiber Size; Web Basis Weight

A nonwoven web provided with a thermally bonded section having a pattern as described below, formed of multicomponent fibers as described above, provides for a hook-and-loop fastening system of relatively high separation resistance. Furthermore, the aforementioned nonwoven web may exhibit high bulkiness as well as excellent softness. Also, the multicomponent fiber configuration may exhibit excellent spinnability and excellent anti-flocking property. Therefore, high productivity may be achieved, and in particular, flocking may be controlled at the time of thermal bonding finish, and high-speed processing may be facilitated.

The nonwoven web formed of the above-described crimped multicomponent fibers does not require specially designed spinning equipment; standard multicomponent hot-melt spinning equipment and methods may be used. In some examples, a spun-bonded nonwoven web produced by spun-bonding method with high productivity is especially desirable.

Production of a spun-bonded nonwoven web of multicomponent fibers may be achieved, in some examples, when the first polymer that forms one area of the multicomponent fiber and the second polymer that forms the other area are melted by separate extruders. The first polymer and the second polymer may be extruded from a nozzle plate having a multicomponent spinning nozzle structure in such a manner that each molten material may be extruded while forming a desired fiber structure so as to extrude a multicomponent long fiber. The long fiber extruded may be chilled by cooling air. In some examples, tension is applied by blowing air to form a predetermined fiber size. The fibers may be deposited and collected as formed, on a collection belt, to create a batt of predetermined thickness. Thickness may be adjusted by adjusting the linear speed of the collection belt. For bonding treatment, thermal bonds may be applied to the batt using thermal bonding equipment. The average fiber size (cross-sectional diameter for fibers of circular cross section, or greatest cross-sectional dimension for fibers of non-circular cross section) of the multicomponent fibers forming the nonwoven web is preferably in the range of 0.2 μm to 100 μm, more preferably 1 μm to 50 μm, and even more preferably 10 μm to 25 μm.

The basis weight of the multicomponent fiber nonwoven web, in some examples, may be in the range of 5 gsm to 80 gsm, or any individual number within the range, or more preferably, 10 gsm to 60 gsm, or still more preferably, 20 gsm to 50 gsm.

Bonding; Bond Patterns

"Line Segment" Patterns

The thermal bonding finish may be achieved using a standard thermal bonding roll. For example, an engraved roll corresponding to the bonding pattern may be used for at least one of a pair of bonding rolls. A nonwoven web may be passed through the nip between the rolls. One or both rolls may be heated, and a combination of compression and heating energy may be applied at the nip. In accordance with the above mentioned properties, etc., required for the nonwoven web produced, temperature, contact pressure, etc., of the rolls may be adjusted for the degree of compression and heating.

Figure 2B:
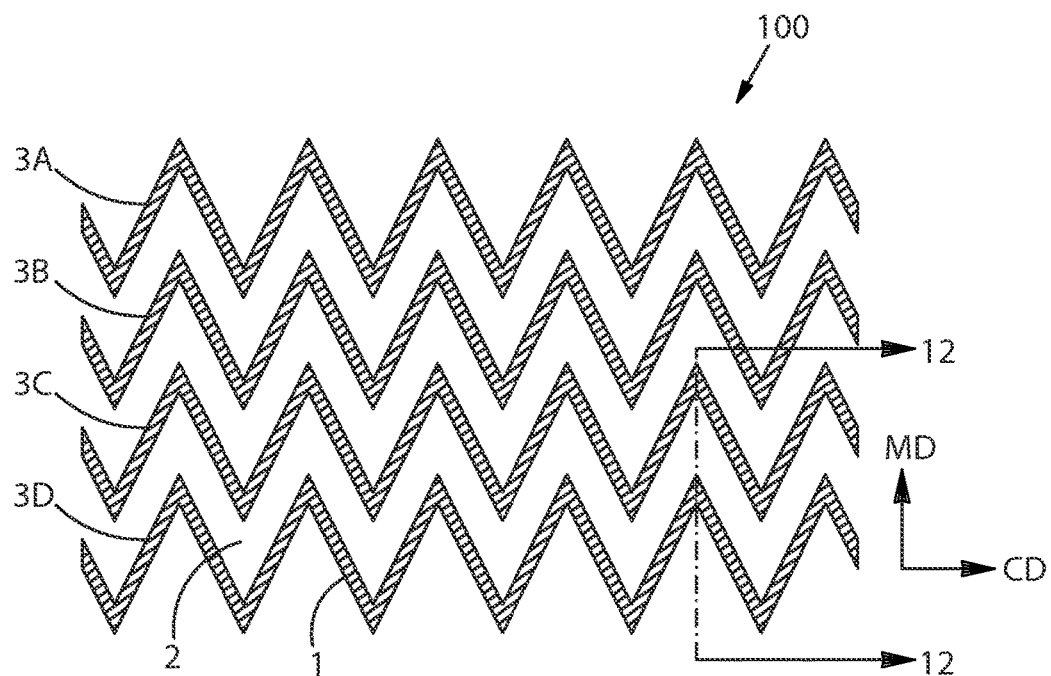
FIG. 2B is a partial top view of an example of a nonwoven web that may be suitable for use as the loops component of a fastening system.
Figure 3:
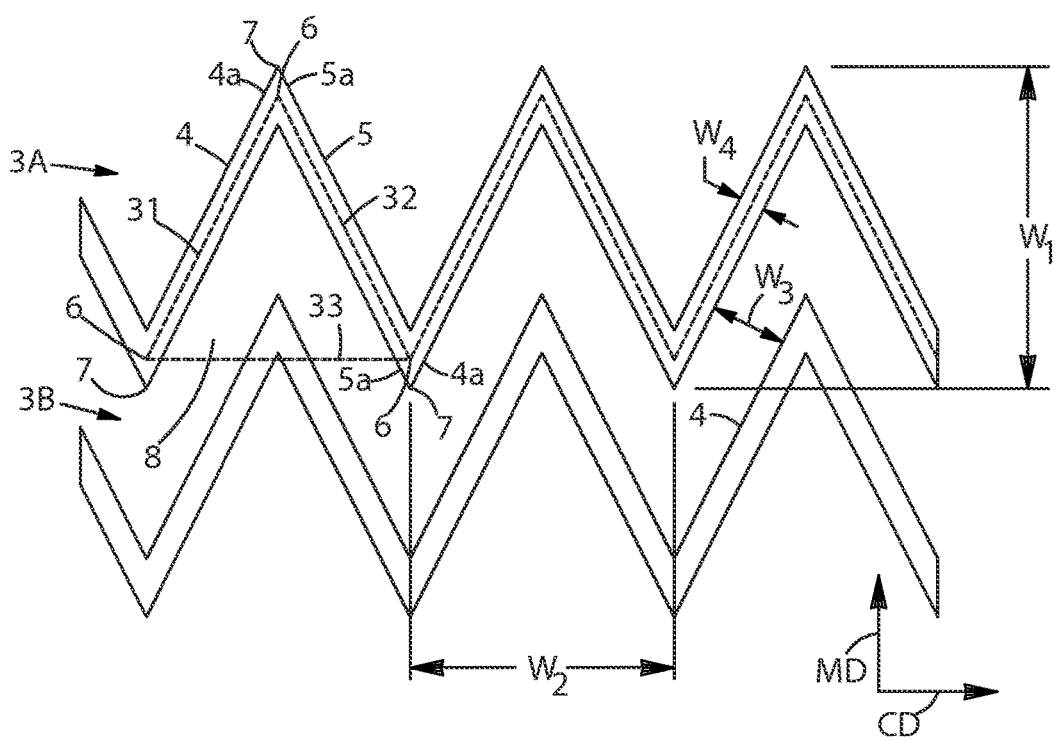
FIG. 3 is an enlarged partial view of the nonwoven web of FIG. 2B.

The thermally bonded pattern of the nonwoven web that may be suitable for use as the loops component of the fastening system contemplated is explained below. As shown in FIG. 2B a partial top view of an example of a nonwoven web that may be suitable for use as the loops component of a fastening system, and FIG. 3 is an enlarged view of the nonwoven web of FIG. 2B.

In FIG. 2B, thermally bonded sections 1, shown by the shaded area correspond to the area where the crimped multicomponent fiber is thermally compressed by thermal bonding rolls. Non-thermally bonded sections 2, correspond to the area between thermally bonded sections 1, and represent the area where thermal compression is not applied to the crimped multicomponent fiber. In the non-thermally bonded sections 2, the crimped multicomponent fiber forms loops that undergo an engagement with the hooks component during fastening of the fastening system.

Figure 12:
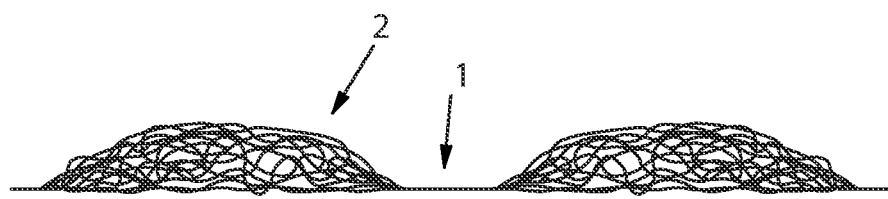
FIG. 12 is a vertical cross sectional view of a portion of an example of a nonwoven web that may be suitable for use as a loops component of a fastening system.

As shown in FIG. 12, the cross section of the nonwoven web that may be suitable for use as the loops component of a fastener shows recessed thermally bonded portion 1 and the non-thermally bonded portion 2. In some examples, the average difference in height or caliper between the non-thermally bonded portion 2 and thermally bonded portion 1 may be in the range of about 0.1 to about 2 mm. The shape of the cross section of the raised area of the engrave of the thermal bonding roll used for formation of thermally bonded portion 1 is not especially limited, and any suitable shape, trapezoidal, for example, may be used.

As shown in FIG. 2B, in some examples, thermally bonded portion 1 in the nonwoven web may comprise a thermally bonded pattern where continuous zigzag unit patterns 3A, 3B, 3C, and 3D, are arranged in the machine direction (MD) at predetermined intervals substantially parallel to the cross direction (CD) of the thermal bonding roll. Examples comprising more than four zigzag unit patterns and less than four zigzag unit patterns are contemplated. As shown in FIG. 3, in some examples, a plurality of unit patterns 3A and 3B may each form a zigzag path having a plurality of first segments 4 and a plurality of second segments 5 arranged in alternating fashion, each slanted at one or more angles with respect to the machine direction. As shown, in some examples, the first segments 4 and the second segments 5 may be substantially straight and may connect at adjacent ends 4a and 5a.

As reflected in FIGS. 2b, 3, 4 and 5, in some examples, the first segments 4 and the second segments 5 may intersect such that no portion of the first segment 4 and no portion of the second segment 5 extend beyond the segment with which it intersects. A common point 6 within or defining first segment 4 and second segment 5 can exist. Referring to unit pattern 3, for example, a common point 6 lies at the intersection between a first centerline 31 and a second centerline 32 of the two segments. The first centerline 31 may lie within in the first segment 4, and the second centerline 32 may lie within the second segment 5. Each of the first segments 4 and second segments 5 may have a centerline.

Apexes 7 may be spatially displaced away from the common points. Again referring to unit pattern 3, apex 7 lies at the outermost point of either first segment 4 or the second segment 5 which ever comprises the outermost point of the unit pattern being referenced.

As shown in FIG. 3, a portion of an adjacent unit pattern, e.g. unit pattern 3B may lie within a triangle 8 formed by three adjacent common points 6 of the first segment 4 and the second segment 5 of the unit pattern 3A. For example, the first centerline 31 of the first segment 4 can form one leg of the triangle 8. Another leg of the triangle 8 may be formed by the second centerline 32 of the second segment 5. A base 33 of the triangle 8 may be a line, which is generally parallel to the Cross direction, between two common points 6 which are spaced apart laterally.

A unit pattern may have a first unit width $W_1$ and a second unit width $W_2$. The first unit width $W_1$ may be measured, in the example shown, as the maximum linear distance, parallel to the machine direction, between the apexes 7. The second unit width $W_2$ may be measured, in the example shown, as the maximum linear distance, parallel to the cross direction, between immediately neighboring and similarly oriented apexes 7, or immediately neighboring common points 6 within similarly oriented segments 4, 5. The second unit width $W_2$ is the inverse of the unit pattern's repeat frequency along the cross direction.

In some examples, a ratio of $W_1/W_2$ may be in the range of about 0.1 to about 10, or any individual number within the range. In some examples, the ratio may be in the range of about 0.5 to about 2.0. In some examples, the width $W_1$ may be in the range of about 3 to about 50 mm or any individual number within the range. In some examples, the width $W_1$ may be in the range of about 5 to about 20 mm.

When any combination of the above-described features is present, a landing zone component may be produced that has relatively high mechanical strength and provides for a fastening system having relatively high separation resistance. In particular, it is desirable for the loops component of the fastener to provide high separation resistance and high mechanical strength in the cross direction, and overlapping of adjacent unit patterns 3A and 3B in the machine direction such that a part of the unit pattern 3B is disposed inside the triangle 8 formed by the three adjacent common points 6 of the unit pattern 3A. The overlapping appears to have a significant effect on strength and separation resistance.

Still referring to FIG. 3, separation distance $W_3$ is the distance between a first segment 4 of the unit pattern 3A and the nearest first segment 4 of the nearest neighboring unit pattern 3B. Separation distance $W_3$ is generally perpendicular to the first segment 4 of the unit pattern 3A and/or the first segment 4 of the neighboring unit pattern 3B. In some examples, distance $W_3$ between neighboring unit patterns 3A and 3B may be in the range of about 1 to about 20 mm, or any individual number within the range. In some examples, separation distance $W_3$ may be in the range of about 2 to about 8 mm.

In some examples, the segment width $W_4$ of segments 4, 5 may be in the range of about 0.5 to about 1.5 mm. Width $W_4$ is measured along a direction perpendicular to the first centerline 31 and second centerline 32 of the first segment 4 and second segment 5, respectively. The width of the remainders of the first segments 4 and second segments 5 of the unit pattern being measured should be taken and averaged.

In some examples, the thermally bonded area ratio (the value obtained by multiplying 100% by the ratio of the area of thermally bonded portion 1 to the total area including thermally bonded portion 1 non-thermally bonded portion 2) may be in the range of about 10 to about 50%. It may be more desirable that the thermally bonded area ratio be in the range of about 20 to about 30%, for better combination of sufficient availability of loops structures (that are engageable by hooks) formed by fibers that have both free portions and bonded portions that are securely bonded down within the web, and web mechanical strength.

In some types of nonwoven web manufacturing processes, fibers are spun and directed to a belt below moving along the machine direction, where they land and accumulate to form a batt on the belt, in a continuous process. The rate of spinning of the fibers and the machine direction speed of the belt may be regulated to control the extent of accumulation of the fibers, thus regulating the basis weight and caliper of the nonwoven web product. Depending upon the rate of spinning and the machine direction speed of the belt, the fibers in the batt and in the finished nonwoven web may tend to have a machine direction bias. In this event, it may be desirable that the bond pattern comprise shapes that have a cross direction bias, to increase the likelihood that each individual fiber in the web will be captured by a plurality of bonds, thereby forming a fiber loop structure between bonds, which provides an engagement structure for a hook in a hooks patch. Accordingly, bond shapes may have a machine direction dimensional component and a cross direction dimensional component, and the bond pattern may be such that the bonded area (i.e., the area occupied by thermally bonded portions 1 as seen in FIG. 12) is occupied predominately by bond shapes having machine direction dimensional components that are greater than their cross direction dimensional components.

When a combination of the above-described features is present, production of a nonwoven web with relatively high mechanical strength as well as high bulkiness, that provides for a fastening system with relatively high separation resistance, is made possible.

Figure 4:
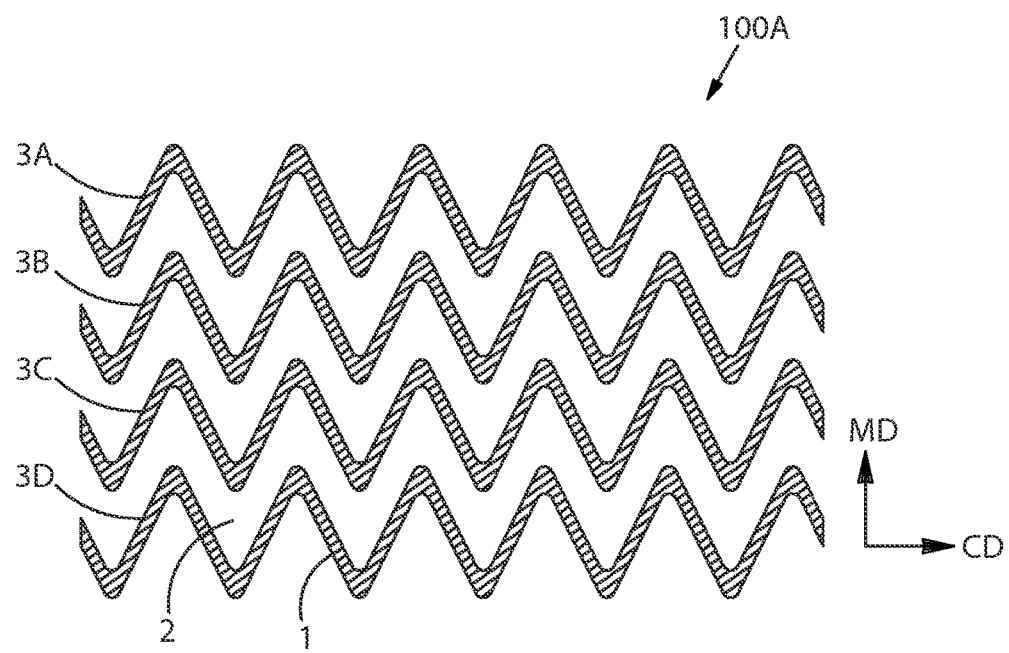
FIG. 4 is a partial top view of another example of a nonwoven web that may be suitable for use as the loops component of a fastening system.
Figure 5:
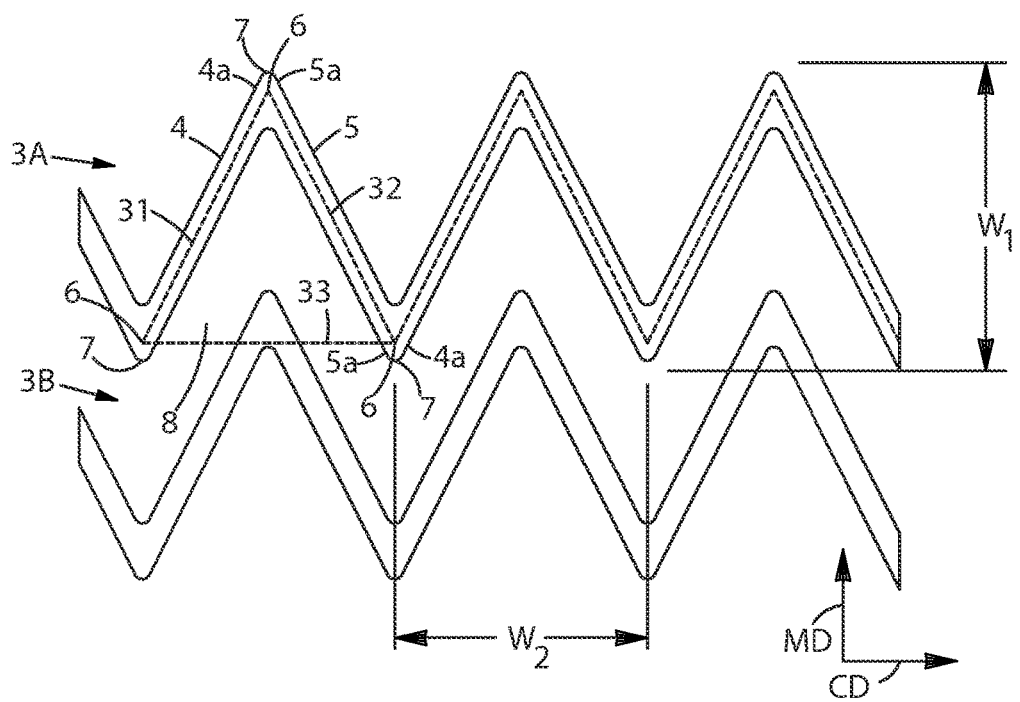
FIG. 5 is an enlarged partial view of the nonwoven web of FIG. 4.

FIG. 4 shows another example of a nonwoven web that may be suitable for use as the loops component of a fastening system contemplated. FIG. 5 is a partially enlarged view of the nonwoven web of FIG. 4. It should be noted that the components corresponding to FIGS. 2 and 3 are indicated by the same codes for FIGS. 4 and 5.

The nonwoven web 100A, in some examples, may have the same structure described previously. For example, as shown in FIG. 4, the nonwoven web 100A may be provided with thermally bonded portion 1 where a plurality of continuous zigzag unit patterns 3A, 3B, 3C, and 3D, are generally parallel to the cross direction of the thermal bonding roll and are arranged in the machine direction at predetermined intervals. In contrast to the nonwoven web 100 discussed with regard to FIGS. 2B and 3, the nonwoven web 100A, in some examples, may comprise a unit pattern, e.g. 3A and 3B, comprising curves at apexes 7.

Figure 6:
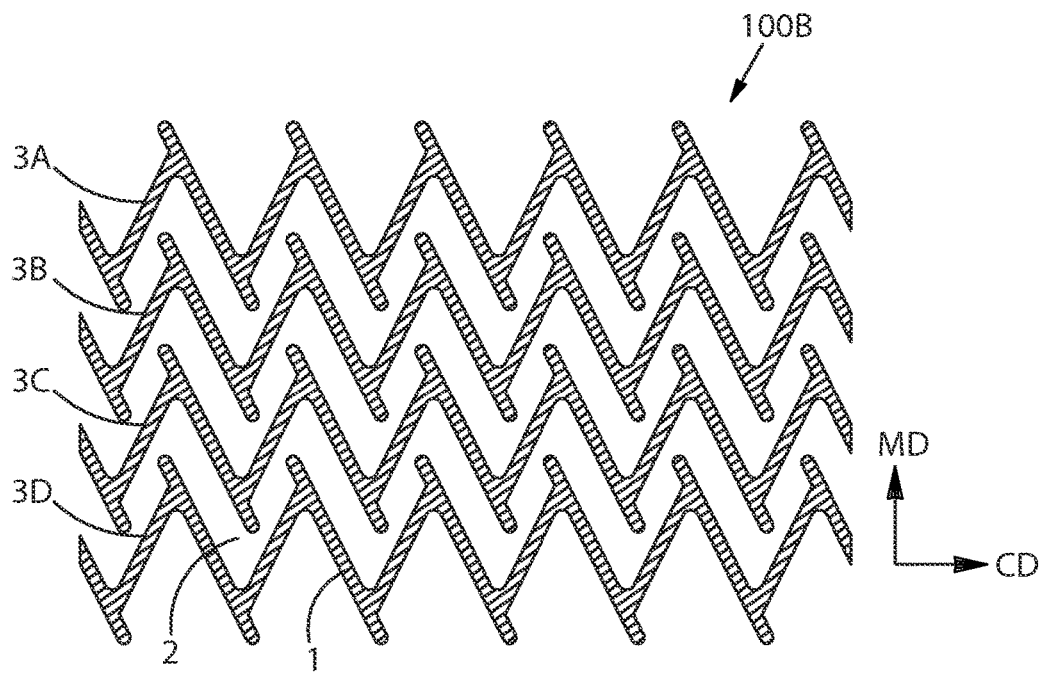
FIG. 6 is a partial top view of another example of a nonwoven web that may be suitable for use as a loops component of a fastening system.
Figure 7:
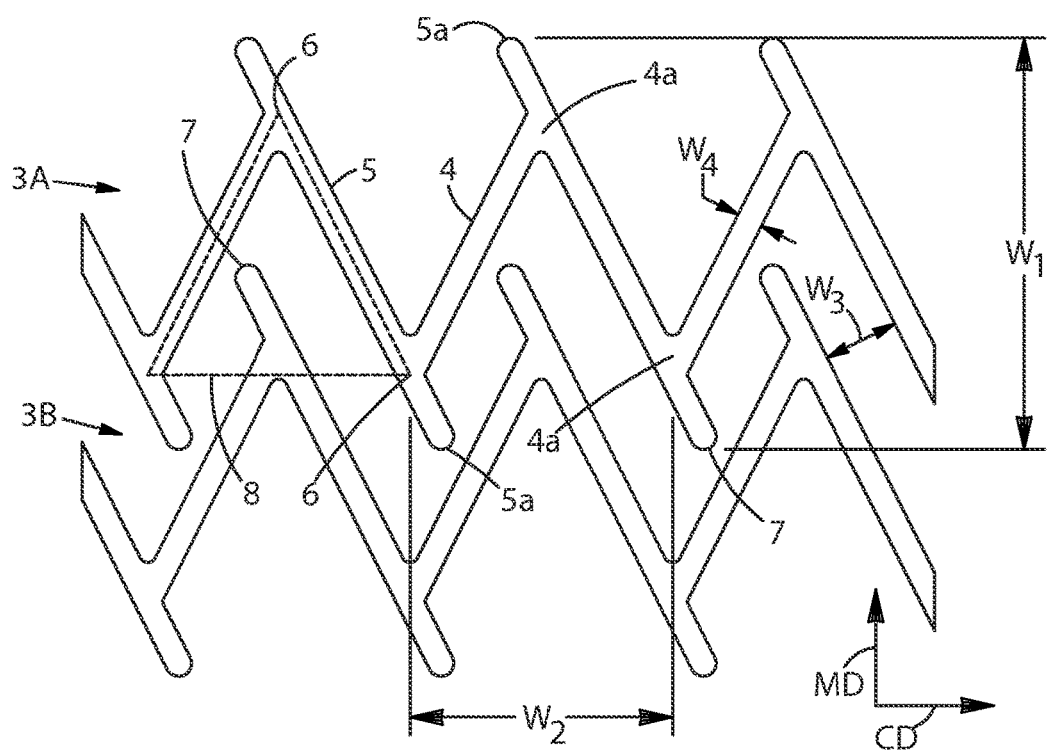
FIG. 7 is an enlarged partial view of the nonwoven web of FIG. 6.

FIG. 6 is a partial top view of another example of a nonwoven web that may be suitable for use as the loops component of a fastening system contemplated, and FIG. 7 is a partially enlarged view of the nonwoven web of FIG. 6. It should be noted that the components corresponding to FIGS. 2 and 3 are indicated by the same codes for FIGS. 6 and 7.

The nonwoven web 100B, in some examples, may have the same structure described previously. For example, as shown in FIG. 6, is the nonwoven web 100B may be provided with thermally bonded portion 1 comprising a plurality of continuous zigzag unit patterns 3A, 3B, 3C, and 3D, generally parallel to the cross direction of the thermal bonding roll and arranged in the machine direction at predetermined intervals.

As shown in FIG. 7, unit patterns 3A and 3B may form zigzag patterns in which first segments 4 are arranged at an angle with respect to the cross direction and slanted to one side at substantially the same angle with respect to the machine direction and second segments 5 are alternately arranged at an angle with respect to the cross direction and slanted toward the other side with respect to the machine direction. The angles at which segments 4 and 5 are arranged with respect to the machine direction may be the same, or they may differ.

As shown, in some examples, the second segment 5 can extend beyond the common point 6. For example, as shown, the end 5a can extend beyond the point of intersection between the first segment 4 and the second segment 5. For example, as shown, the apexes 7 correspond to the outermost points of the second segment 5 of the unit pattern 3A. Because the end 5a extends beyond the intersection between the first segment 4 and the second segment 5, the common point 6 is disposed inward from the apex 7. In other examples, the apexes 7 may be the outermost points of the first segment 4.

As shown in FIG. 7, a portion of unit pattern 3B may be disposed within the triangle 8 formed by three adjacent common points 6 of the unit pattern 3A. For the examples shown in FIGS. 6 and 7, the ratio $W_1/W_2$ may be in the range of about 0.1 to about 10, or any individual number within the range, in some examples. In some examples, the ratio may be in the range of about 0.5 to about 2.0.

When any combination of the above-described features is present, production of a landing zone component having a relatively high mechanical strength in both the machine direction and cross direction, and one that provides a hook-and-loop fastening system with a relatively high separation resistance, may be made.

Figure 8:
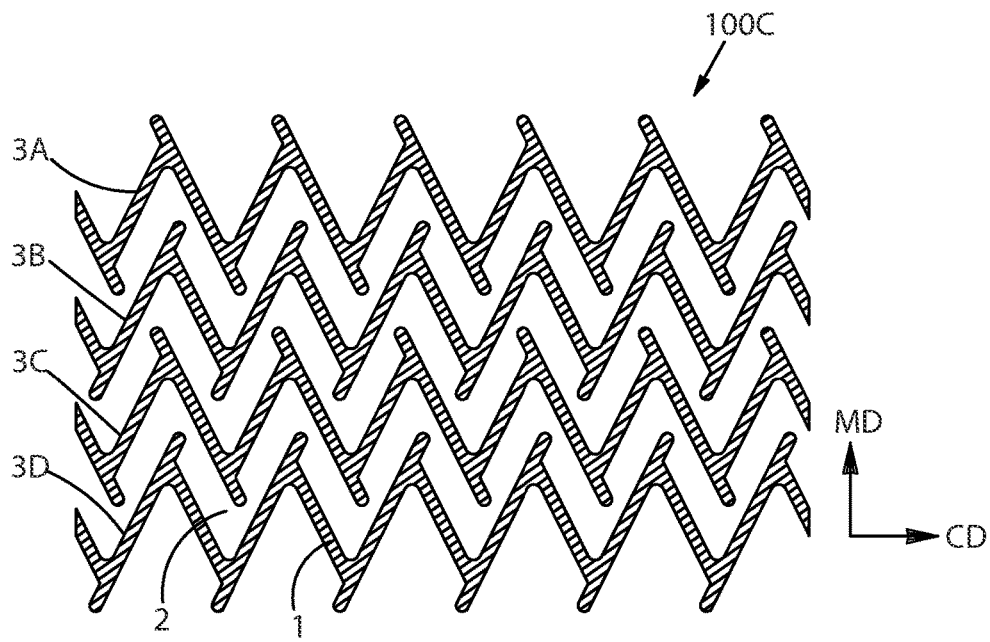
FIG. 8 is a partial top view of another example of a nonwoven web that may be suitable for use as the loops component of a fastening system.
Figure 9:
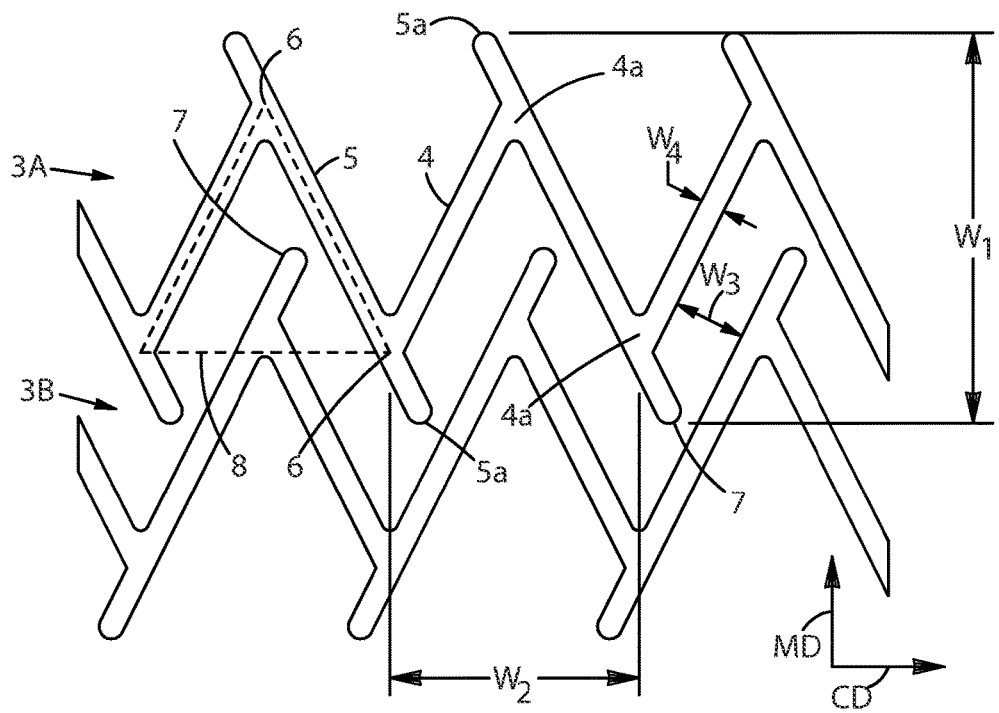
FIG. 9 is an enlarged partial view of the nonwoven web of FIG. 8.

FIG. 8 is a partial top view of another example for a nonwoven web 100C that may be suitable for use as the loops component of a fastening system contemplated, and FIG. 9 is an enlarged partial view of same. It should be noted that the components corresponding to FIGS. 6 and 7 are indicated by the same codes for FIGS. 8 and 9.

The nonwoven web 100C, in some examples, may have the same structure described previously. For example, and as shown in FIG. 8, the nonwoven web 100C may be provided with thermally bonded portions 1 comprising unit patterns 3A, 3B, 3C, and 3D, generally parallel to the cross direction of the thermal bonding roll are arranged in the machine direction at predetermined intervals. In some examples, the first segments 4 can extend beyond the common points 6. In some examples, the second segments 5 can extend beyond the common points 6. In some examples, the unit pattern 3B may comprise first segments 4 which extend beyond the common points 6, while the unit pattern 3A may comprise second segments 5 which extend beyond the common points 6. In yet other examples, a single unit pattern 3 may comprise at least one first segment 4 which extends beyond a common point 6 and at least one second segment which extends beyond a common point 6.

For example, as shown in FIG. 9, the nonwoven web 100C, may comprise, in some examples, the unit pattern 3A having a shape where the end 5a of the second segment 5 extends beyond common point 6, and the unit pattern 3B having a shape where the end 4a of the first segment 4 extends beyond common point 6. The unit patterns may be arranged alternately in the machine direction. As shown, in some examples, the first segment 4 and the second segment 5 may be mutually connected with end 4a of the first segment 4 and the adjacent end 5a of the second segment 5.

As shown, a part of unit pattern 3B may be disposed within the triangle 8 formed by adjacent three common points 6 of the first segment 4 and the second segment 5 in unit pattern 3A. In some examples, the end 5a of the second segment 5 of the unit pattern 3A may be contained inside a triangle formed by three adjacent common points 6 of an adjacent unit pattern.

When structured with any combination of features as described above, production of a landing zone component providing suitable fastening strength expressed as separation resistance, as well as high mechanical strength in both the machine direction and cross direction may be made.

Figure 10:
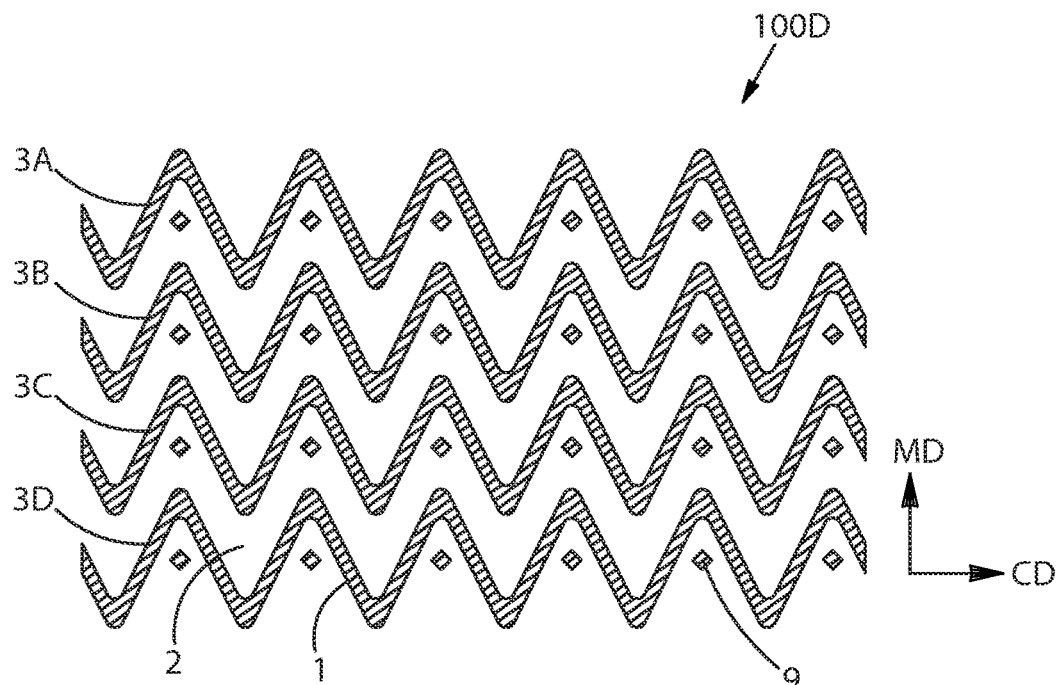
FIG. 10 is a partial top view of another example of a nonwoven web that may be suitable for use as a loops component of a fastening system.
Figure 11A:
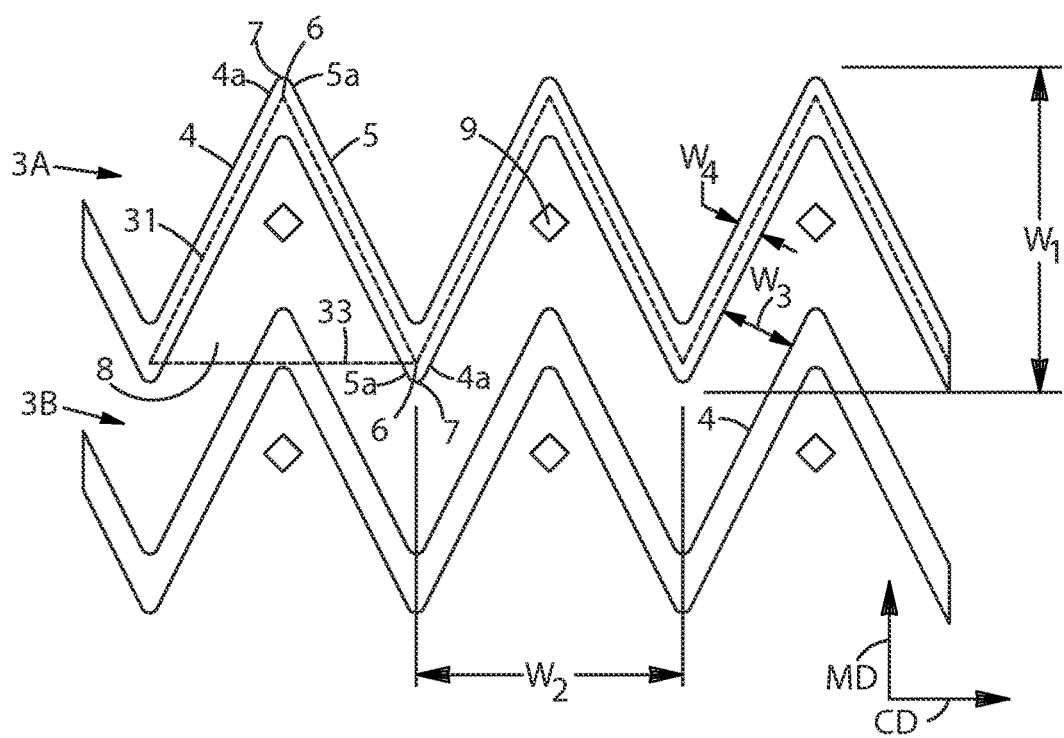
FIG. 11A is an enlarged partial view of the nonwoven web of FIG. 10.

FIG. 10 is a partial top view of another example of a nonwoven web 100D that may be suitable for use as the loops component of a fastening system contemplated, and FIG. 11A is a partially enlarged view of same. It should be noted that the components corresponding to FIGS. 2 and 3 are indicated by the same codes in FIGS. 10 and 11A.

The nonwoven web 100D, in some examples, may have the same structure described previously. For example, the nonwoven web 100D may be provided with a thermally bonded portion 1 comprising unit patterns 3A, 3B, 3C, and 3D, generally parallel to the cross direction of the thermal bonding roll which are arranged in the machine direction at predetermined intervals.

As shown in FIG. 11A, in some examples, the unit patterns 3A and 3B may comprise a zigzag pattern where first segments 4 are arranged at an angle with respect to the cross direction and slanted to one side at substantially the same angle with respect to the machine direction. Additionally, as shown, in some examples, the unit patterns 3A and 3B may further comprise second segments 5 arranged at an angle with respect to the cross direction and slanted toward the other side with respect to the machine direction at substantially the same angle. As shown, in some examples the first segments 4 and the second segments 5 may be arranged alternately. The first segment 4 and the second segment 5 may be mutually connected with the end 4a of the first segment 4 and the end 5a of the second segment 5 as the common point 6.

As shown in FIG. 11A, a part of unit pattern 3B may be disposed within the triangle 8 formed by adjacent three common points 6 of the first segment 4 and the second segment 5 (triangle 8 indicated by the dotted lines in FIG. 11A) of the unit pattern 3A.

In some examples, a ratio of $W_1/W_2$ may be, in the range of about 0.1 to about 10, or any individual number within the range. In some examples, the ratio may be in the range of about 0.5 to about 2.0 as explained above.

Also, as shown, in some examples, a dot pattern 9 may be disposed between the unit patterns 3A and 3B. For example, as shown, in some examples, the dot pattern 9 may be disposed within the triangle 8. In some examples, the dot pattern 9 may be formed by thermal compression by a thermal bonding roll. In these examples, the thermally bonded portion of the thermal bonding roll may comprise unit pattern 3 and also dot pattern 9.

The position of dot pattern 9 may be any suitable position between the unit patterns 3A and 3B. The shape of dot pattern 9 may be any suitable shape. Examples of some suitable shapes include dots, ellipses, squares, rectangles, triangles, polygons, crescent, star, and the like. In some examples, the size of the dot is determined by taking factors such as fastening strength and bulkiness into consideration.

"Wavy" Patterns

Figure 11B:
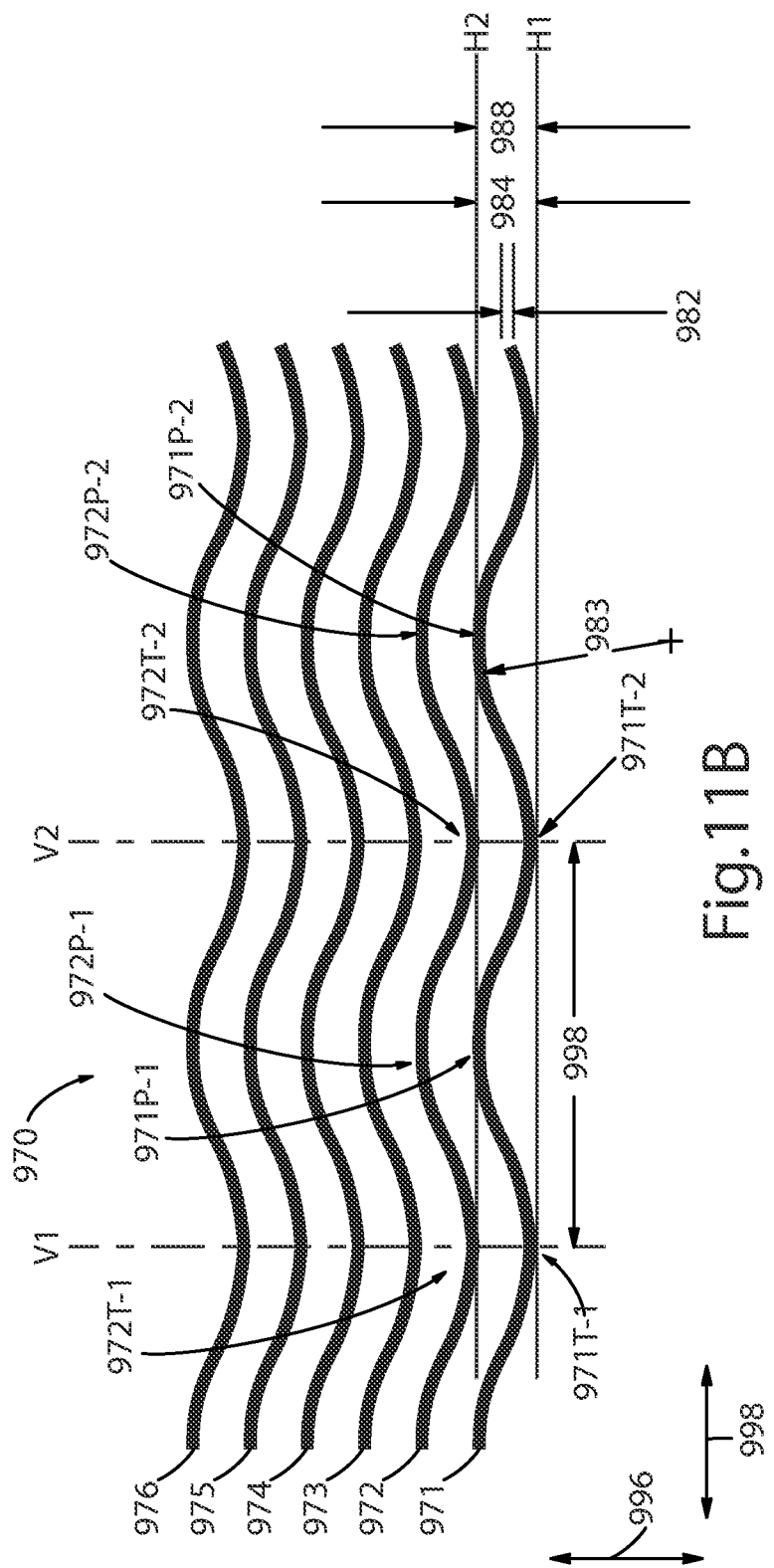
FIG. 11B is partial view of another example of a bond pattern.

FIG. 11B illustrates a top view of a portion of another example of a bond pattern 970 for a nonwoven landing zone. The bond pattern 970 includes a longitudinal direction 996 and a lateral direction 998. The bond pattern 970 can be applied to a nonwoven landing zone such that the longitudinal direction 996 coincides with a machine direction of the nonwoven material of the landing zone and the lateral direction 998 coincides with a cross direction of the nonwoven material. In alternate examples, the bond pattern 970 can be angled, such that the longitudinal direction 996 is at an angle with respect to a machine direction of the nonwoven material of the landing zone. For example, a bond pattern may be angled at an angle of 0.26° with respect to a machine direction of the nonwoven material of the landing zone, in order to provide certain contact conditions between equipment and material during a bonding process, as will be understood by one of ordinary skill in the art.

The bond pattern 970 includes a plurality of bond lines 971, 972, 973, 974, 975, and 976. In FIG. 11B, the bond lines are illustrated as having thickness. The bond lines 971-976 can be thermal bonds or ultrasonic bonds or any other kind of bonds for bonding a nonwoven material. While each of the bond lines 971 through 976 is configured in the same way, this description will specifically refer to the details of bond lines 971 and 972 for ease of reference. In some examples, a bond pattern can include one or more bond lines that differ from the other bond lines in the pattern. The differing bond line(s) can differ in any way described herein. As used herein, the term "bond line" is intended to mean a recognizable pathway, formed by one or more bonded areas, and having a defined width that is substantially less than a defined length.

A bond pattern with a number of bond lines having a wavy shape is considered more useful than a bond pattern with a series of parallel bond lines having a straight line shape because straight lines would be unlikely to bond nonwoven fibers in some orientations. For example, a series of parallel bond lines oriented in the cross-direction on a nonwoven material would be unlikely to catch nonwoven fibers primarily oriented in the cross-direction and disposed between the bond lines. As a result, these unbonded fibers would offer reduced strength loops and thus a hook and loop fastening system with reduced performance. Thus, examples of the present disclosure contemplate bond patterns with a number of bond lines having a wavy shape. As used herein, the term "wavy" is intended to mean a non-linear shape that has at least some minimal amplitude along its length; that is, a wavy shape deviates from its overall course by more than one thickness of its pathway. In various examples, a wavy shape can be continuously curved, can be partially curved and partially linear, or can be formed from a series of connected linear segments, such as a zig-zag pattern.

The bond line 971 is a continuous wavy line formed by a repeating pattern of identical waves. However, in various examples, a bond line can be a discontinuous line, or an effective line formed by a number of lines segments, or an effective line formed by a series of spaced apart bond areas. Also, in some examples, the waves may not be identical. The present disclosure contemplates that each wave in each bond line can vary in any way described herein.

In the bond pattern 970, the waves of each of the bond lines 971-976 are formed by an alternating series of peaks and troughs. In the illustrated portion of the pattern 970, the bond line 971 includes a first trough 971T-1 followed by a first peak 971P-1 followed by a second trough 971T-2 followed by a second peak 971P-2, and so on. The bond line 971 has a constant wave amplitude 984 measured longitudinally from top of peak to bottom of trough and a constant wavelength 986 measured laterally from a trough to an adjacent trough (or from a peak to an adjacent peak). In alternate examples, a bond line can have a varying wave amplitude and/or wavelength. The bond line 971 is continuously curved with an inside radius 983 on each peak and trough. In the example of FIG. 11B, each of the other bond lines 972 through 976 also has the constant wave amplitude 984, the constant wavelength 986, and the inside radius 983.

The bond line 972 is configured in the same way as the bond line 971. Thus, the bond line 972 includes a first trough 972T-1, a first peak 972P-1, a second trough 972T-2, and a second peak 971P-2. The bond line 972 also has the constant amplitude 984 and the constant wavelength 986. In the lateral direction, the bond line 972 is in phase with the bond line 971, such that the peaks of the bond line 972 are aligned with the peaks of the bond line 971. The troughs of the bond lines 971 and 972 are similarly aligned. However, in various examples, one or more bond lines can be out of phase.

Line V1 is a longitudinally oriented reference line drawn through the bottom of the first trough on each of the bond lines 971 through 976. Line V2 is a longitudinally oriented reference line drawn through the second trough on each of the bond lines 971 through 976. Since the bond lines 971 and 972 are in phase, the first trough 971T-1 and the first trough 972T-1 are both aligned on line V1. Since the bond lines 971 and 972 have the same wavelength 986, the second troughs 971T-2 and 972T-2 are aligned on line V2. Each of the other bond lines 973 through 976 is aligned in the same way with bond lines 971 and 972, as well as with each other.

The bond line 971 has a constant bond line width 982. Each of the other bond lines 972 through 976 has the same constant bond width. However, in some examples, a bond line width can vary along a bond line or from one bond line to another.

The bond line 972 is longitudinally offset from the bond line 971 by a pitch 988 measured longitudinally from top of peak on bond line 971 to top of peak on bond line 972 (or bottom of trough to bottom of trough, respectively). Each of the other bond lines 973 through 976 is longitudinally offset from the adjacent bond line by the same pitch 988 to create a regular array of bond lines in the bond pattern 970. As a result, all of the bond lines 971-976 are non-intersecting with respect to each other. In some alternate examples, a bond pattern can include bond lines offset from each other with varying pitches.

Line H1 is a laterally oriented reference line drawn along the bottoms of the troughs on the bond line 971. Line H2 is a laterally oriented reference line drawn along the tops of the peaks on the bond line 971. In the example of FIG. 11B, the pitch 988 is the same as the amplitude 984. As a result, line H2 is also drawn along the bottoms of the troughs on the bond line 972.

In a bond pattern, the bond line width, the wave amplitude, the wavelength, and the pitch together determine the percent area that is bonded (and the percent area that is unbonded).

In various examples, it may be beneficial to the visual appearance of a printed area overlaid with a bond pattern, to reduce the bond line width while maintaining a target percent bonded area. In order to do so, the pitch of the bond pattern can be reduced, to control the percent bonded area. Without wishing to be bound by this theory, the present disclosure contemplates that a bond pattern with a reduced bond line width and a reduced pitch offers a more homogeneous appearance that is visually pleasing and allows images on the printed area to be more readily visibly discernible from the bond pattern.

For example, a bond pattern can have a bond line width of less than 0.8 mm, but a reduced pitch, in order to maintain a bonded area of at least 20%. As another example, a bond pattern can have a bond line width of less than 0.6 mm, but a reduced pitch, in order to maintain a bonded area of at least 20%. As a further example, a bond pattern can have a bond line width of less than 0.4 mm, but a reduced pitch, in order to maintain a bonded area of at least 20%. As still a further example, a bond pattern can have a bond line width of less than 0.2 mm, but a reduced pitch, in order to maintain a bonded area of at least 20%. Alternatively, these examples can also be implemented with other target percent bonded areas, such as targets of 15% or 25%, or any integer value for a percent between these two values.

However, there are practical lower limits to bond line width and bond pattern pitch. If a bond line width is reduced to a very small dimension (e.g. to about 0.1 mm or less), then some bonding processes may begin tearing or cutting nonwoven fibers rather than properly bonding them. Also, if a pitch of a bond pattern is reduced to a very small dimension (e.g. to about 1 mm or less), then there may be insufficient unbonded nonwoven fibers for forming loops, resulting in a need for much larger (and more expensive hook areas) or resulting in a hook and loop fastening system with reduced performance. These considerations will be understood by one of ordinary skill in the art.

In a particular example, a bond pattern can be configured in the same way as the bond pattern 970, with the following dimensions: a constant bond line width of 0.6 mm, a constant wave amplitude of 3.4 mm, a constant wavelength of 24.42 mm, and a constant pitch of 3.4 mm, resulting in a bonded area of approximately 18%. The present disclosure contemplates variations of this particular example wherein any of the dimensions described above can be varied independent from the others. This particular example can be varied as described below.

One or more bond lines in a bond pattern can have a constant bond line width that can be less than 0.2 mm, or 0.2 mm, or 0.3 mm, or 0.4 mm, or 0.5 mm, or 0.6 mm, or 0.7 mm, or 0.8 mm, or 0.9 mm, or 1.0 mm, or 1.1 mm, or 1.2 mm, or 1.3 mm, or 1.4 mm, or 1.5 mm, or 1.6 mm, or 1.7 mm, or 1.8 mm, or 1.9 mm, or 2.0 mm, or greater than 2.0 mm, or any width between any of these specific values. Alternatively, a bond line width can vary between any of the values described above.

One or more bond lines in a bond pattern can have a constant wave amplitude that can be less than 2.0 mm, or 2.5 mm, or 3.0 mm, or 3.5 mm, or 4.0 mm, or 4.5 mm, or 5.0 mm, or 5.5 mm, or 6.0 mm, or 6.5 mm, or 7.0 mm, or greater than 7.0 mm, or any value between any of these specific values, in increments of 0.1 mm. Alternatively, a wave amplitude can vary between any of the values described above. In various examples, it may be beneficial to the visual appearance of a printed area overlaid with a bond pattern to have a wave amplitude that is low (e.g. less than 10 mm) but non-zero. Without wishing to be bound by this theory, the present disclosure contemplates that a bond pattern having a wave amplitude that is low is visually pleasing, but still avoids the difficulties presented by bond lines having a straight line shape, as discussed above.

One or more bond lines in a bond pattern can have a constant wavelength that can be less than 5 mm, or 10 mm, or 15 mm, or 20 mm, or 25 mm, or 30 mm, or 35 mm, or 40 mm, or 45 mm, or 50 mm, or greater than 50 mm or any integer value in mm between any of these specific values. Alternatively, a wavelength can vary between any of the values described above.

A bond pattern can have bond lines at a constant pitch that can be less than 2.0 mm, or 2.5 mm, or 3.0 mm, or 3.5 mm, or 4.0 mm, or 4.5 mm, or 5.0 mm, or 5.5 mm, or 6.0 mm, or 6.5 mm, or 7.0 mm, or greater than 7.0 mm or any value between any of these specific values, in increments of 0.1 mm. Alternatively, a bond pattern pitch can vary between any of the values described above.

A bond pattern can result in a bonded area that can be less than 10%, or 10%, or 15%, or 20%, or 30%, or greater than 30%, or any integer value in percent between any of these specific percentages.

A bond pattern may be imparted with any of the additional features described in, for example, U.S. patent application Ser. No. 12/783,600. The wavy pattern and particular features described herein and in the cited application may be desirable not only for purposes of enhanced separation resistance, but also for use in conjunction with printed graphics that underlie the nonwoven, for enhanced visibility of the printed graphics.

Other Patterns

It will be appreciated that other bond patterns may be desired in some circumstances as well, including patterns formed of discrete closed shapes. Where the multicomponent fibers have a machine direction bias, however, it may be desired that any such patterns do not leave open a continuous line of unbonded material along the machine direction. Rather, it may be desired that the pattern be configured and arranged such that any line extended along the nonwoven machine direction necessarily encounters a bond at an average frequency of at least 0.5 bond per cm along the machine direction, and more preferably at least 1 bond per cm along the machine direction, and still more preferably at least 1.5 bonds per cm along the machine direction. This attribute will increase the likelihood that every fiber forming the nonwoven is bonded to the nonwoven structure with suitable periodicity, so as not to leave unduly long unbonded portions of fibers (which would not be useful for imparting separation resistance in a hook and loop fastening system).

Other examples of bond patterns that may be useful in conjunction with the multicomponent fiber nonwoven web described herein, to form a component of a hook-and-loop fastening system, are disclosed in U.S. Pat. Nos. 6,296,629; 5,964,742; 5,858,515; 5,318,555; and 5,256,231; and in U.S. Pat. App. Pub. No. US 2003/0077430.

When provided with any combination of the features described above, a landing zone component providing sufficient fastening strength as expressed by separation resistance as well as high mechanical strength in both of machine direction and cross direction may be made.

Multilayer Nonwoven Web with Multicomponent Fiber Layer

The nonwoven web of crimped multicomponent fibers according the description above may form one layer of a multilayer web, in some examples. For example, a nonwoven web of multicomponent fibers may be used as an uppermost layer and may be laminated or otherwise affixed, bonded or associated with one or more other layers of differing composition and/or structure therebeneath. The one or more other layers may be, for example, a monocomponent fiber nonwoven web, a knitted or woven fabric, a paper or cellulose web material, or a polymer film material, combinations thereof, and even sub-multilayer combinations thereof.

Any suitable method may be utilized to create the multilayer web. For example, a nonwoven multilayer web may be produced using a method wherein respective batts of monocomponent and multicomponent fibers are formed separately, and then subsequently bonded together to form a multilayer web, in a single bonding step. In another example, the respective batts may be separately formed and then one or both may be separately pre-bonded to form one or more respective bonded nonwoven web layers, and the respective web layers and/or web layer and unbonded batt layer may be bonded to form a bonded multilayer web.

Figure 18:
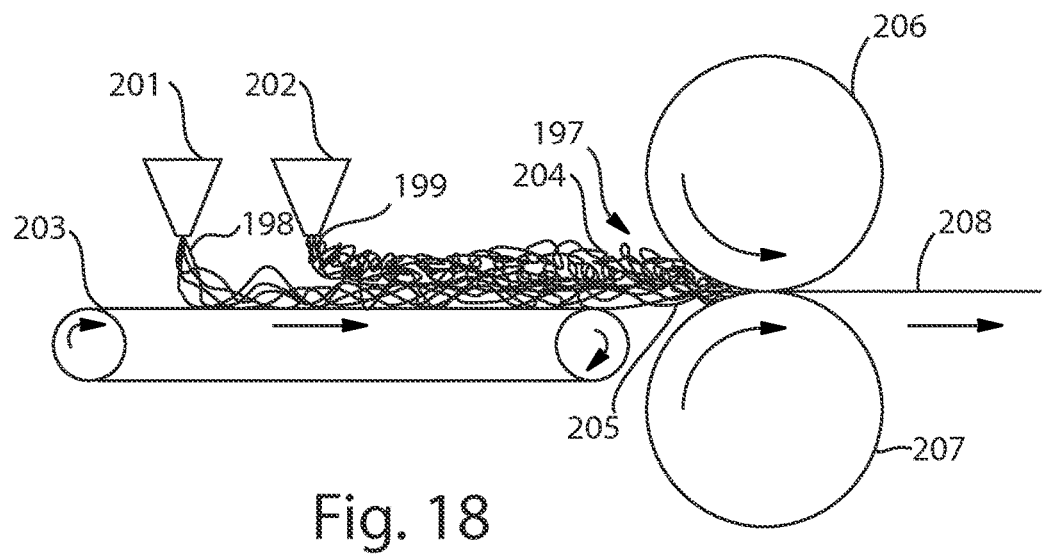
FIG. 18 is a schematic side view of equipment, and depiction of a process, for spinning more than one type of fiber component, creating a batt having layers of more than one type of fiber component, and bonding the batt to form a bonded nonwoven web.

Referring to FIG. 18, in one particular example, a first beam of spinnerets 201 spinning monocomponent fibers 198 may be situated over a moving belt 203, upstream of a second beam of spinnerets 202 spinning crimped multicomponent fibers 199, such that the monocomponent fibers 198 are laid down first and the crimped multicomponent fibers 199 are laid down over the monocomponent fibers, thereby forming a batt 197 having at least two layers 204, 205 of the differing fibers. It will be appreciated that additional beams spinning and depositing additional layers of differing types of fibers may be used to form a multi-layer batt. One or more of the beams, or even all of them, may be configured to spin multicomponent fibers as described herein. It will be appreciated that the order of placement of the respective beams of spinnerets on the line can be configured to affect whether the multicomponent fiber layer(s) will be disposed on the bottom of, the top of, or at an intermediate location within, the batt. Thus, for example, a first nonwoven batt layer formed of monocomponent fibers may be disposed superjacent or subjacent to a second nonwoven batt layer formed of crimped multicomponent fibers. In the example depicted in FIG. 18, the monocomponent fibers are disposed subjacent the multicomponent fibers.

When a multilayer web is to be formed of a multilayer batt including a layer of multicomponent fibers as described herein, and a layer of monocomponent fibers, and the web is to be used as landing zone material for a fastening system as described herein, it may be preferred that the layer of multicomponent fibers be deposited and disposed at the location most proximate the surface of the finished nonwoven web that will face and engage the hooks component of the fastening system. In other words, it may be preferred that the multicomponent fibers form the outermost or uppermost, hook-facing/engaging layer of fibers of the web.

In some circumstances a nonwoven web of a particular minimum basis weight may be desired e.g., for purposes of appearance, while at the same time it is desired to include multicomponent fibers including polyamide sections for enhanced fiber strength and fiber crimp, making them useful as landing zone components. In such circumstances it may be desirable to include a first layer of monocomponent fibers of, e.g., polyolefin such as polypropylene, the first layer having a first basis weight, and a second layer of multicomponent fibers (including polyolefin and polyamide sections) having a second basis weight, wherein the first and second basis weights make up the desired minimum basis weight of the web. This may enable enjoyment of the advantages provided by the multicomponent fibers with polyamide sections, while providing a way to save on the cost of the more expensive polyamide polymer material.

Still referring to FIG. 18, a multilayer batt 197 formed via a multiple-beam process as described above may be subsequently thermally bonded such that thermal bonding of all of the fibers occurs in a single step to form a multilayer nonwoven web. For example, batt 197 may be conveyed into the nip between a pair of bonding rollers 206, 207 which may be configured to bond the multilayer web in a pattern, e.g., any one of the patterns described herein, or other pattern, to form thermally bonded multilayer nonwoven web 208. In other examples, batt 197 may be consolidated by pre-calendering and may be subjected to other processes such as hydroentangling or needle punching to cause the differing fibers in batt 197 to be more evenly distributed, intertangled and/or intertwined, prior to bonding.

Figure 19:
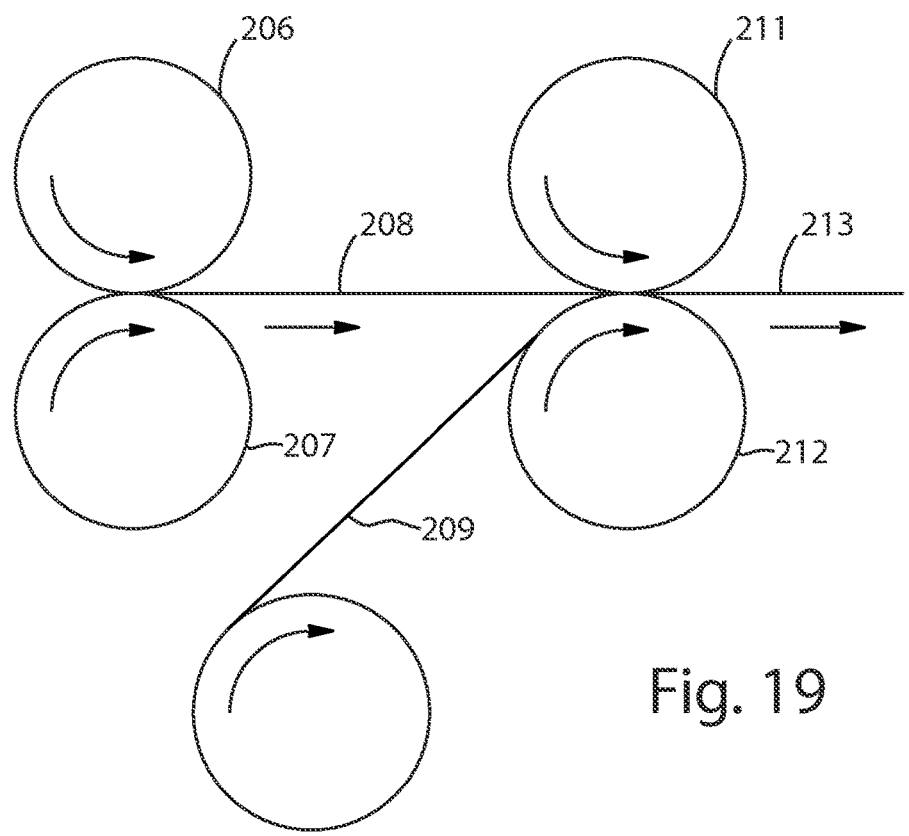
FIG. 19 is a schematic side view of a process for laminating a nonwoven web layer with another nonwoven web or other layer to form a multilayer laminate web.

In another alternative, the multilayer web may be produced using a method where lamination is done following the bonding of individual batts of fibers to form individual nonwoven webs. For example, a first batt may be formed of monocomponent fibers and then consolidated and thermally bonded in a bond pattern to form a first monocomponent fiber nonwoven web. A second batt may be formed of multicomponent fibers and then consolidated and thermally bonded (e.g., according to one of the bond patterns described herein) to form a second multicomponent nonwoven fiber web. Following that, the first and second nonwoven webs may be laminated together, by themselves or with additional nonwoven web, fabric and/or film layers by any suitable method, using, e.g., additional thermal bonding lamination, adhesive lamination, or any other suitable method for laminating and bonding web layers. In some examples, layers in addition to the multicomponent fiber nonwoven web as described herein may include spunbond nonwoven webs, meltblown nonwoven webs, carded nonwoven webs, knitted or woven fabrics, polymeric films, etc. For example, referring to FIG. 19, a thermally bonded web 208 may be further laminated with an additional web 209 between a pair of laminating rollers 211, 212, to form laminate multilayer web 213. Additional web 209 may be another nonwoven web such as a spunbond nonwoven web, meltblown nonwoven web, or carded nonwoven web, which itself may have been thermally bonded in a pattern. Alternatively, additional web 209 may be a knitted or woven fabric, a polymeric film, a cellulose pulp-based fibrous web (e.g., paper) etc. Rollers 211, 212 may be thermal bonding rollers, or may be merely compressing/consolidating rollers, wherein lamination bonding is accomplished by compression and use of an adhesive applied between webs 208 and 209.

Material Forming Monocomponent Fiber Layer

Polymers that may be used to form the monocomponent fibers of a monocomponent fiber layer may be polyolefins, polyesters, polyamides, polyurethanes, etc. Suitable examples of polyolefins include propylene, polyethylene, and mixtures of the same. From the standpoint of spinnability, heat-resistance, and thermal fusion property, propylene/polypropylene may be preferred, particularly when the monocomponent fiber layer is to be thermally bonded with a multicomponent fiber layer, in which the multicomponent fibers have propylene/polypropylene components. Other polymers that are used to form one of the component sections of the multicomponent fibers described above may be used to form the fibers of a monocomponent fiber nonwoven batt/web layer as well.

In other examples, when a melt-blown nonwoven web will form the monocomponent fiber layer, use of polypropylenes with a melt-flow rate in the range of about 30 to about 3000 g/10 min, or any individual number within the range may be used. As another example, polypropylenes having a melt-flow rate in the range of about 400 to about 1500 g/10 min may be used. In some examples, the use of polypropylenes with the ratio of weight-average molecular weight to number-average molecular weight Mw/Mn may be in the range of about 2 to about 6.

Furthermore, for polyethylene, homopolymers of ethylene (either low-pressure method or high-pressure method may be used for production) and copolymers of ethylene and other α-olefins may be used for production. Suitable α-olefins include α-olefins with 3-20 carbon atoms such as propylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene. The α-olefins may be used independently for copolymerization or two or more different types may be used in combination for copolymerization.

In some examples, polyethylene may have a density in the range of about 880 to about 970 kg/m$^2$, or any individual number within the range. In some examples, the density may be in the range of about 910 to about 965 kg/m$^3$. In the case of a melt-blown nonwoven web, in some examples, the melt flow rate may be in the range of about 10 to about 400 g/10 min or any individual number within the range. In some examples, the melt flow rate may be in the range of about 15 to about 250 g/10 min. The melt flow rates are determined in part while the samples are under a temperature of 190° C. and load of 2160 g. Also, in some examples, the nonwoven web may have a ratio of the weight-average molecular weight to number-average molecular weight, Mw/Mn, in the range of about 1.5 to about 4.

Furthermore, for polyesters, aromatic polyesters having excellent strength, rigidity, etc., or biodecomposable aliphatic polyesters may be used for production. Suitable examples of aromatic polyesters include polyethylene terephthalate, polytrimethylene terephthalate, polytetramethylene terephthalate, etc. Suitable examples of aliphatic polyesters include polycondensates of a polyhydric carboxylic acid such as malonic acid, succinic acid, glutaric acid, adipic acid, sebacic acid, dodecanoic acid, malic acid, tartaric acid and citric acid and a polyhydric alcohol such as ethylene glycol, propylene glycol, butanediol, hexanediol, glycerol, and trimethylolpropane, ring-opening polymers such as lactide and caprolactone, and polycondensates of lactic acid, hydroxy acids such as hydroxybutyric acid and hydroxyvaleric acid, etc.

When the layers of a multilayer web including a multicomponent fiber nonwoven layer are to be joined/laminated by means other than thermal bonding after spinning (e.g., by use of adhesive), selection of the material(s) forming the layer(s) to be joined to the multicomponent fiber nonwoven layer is not especially limited. For example, a layer comprising a knitted fabric, woven fabric, nonwoven web of any composition, polymer film, etc., may be used. As for the lamination method, a thermal fusion process such as thermal bonding finish, ultrasonic fusion, mechanical webbing methods such as needle punching and water jetting, adhesion with a hot-melt adhesive, etc., extrusion lamination when a film, etc., may be used.

The nonwoven web that may be suitable for use as the loops component of a fastening system contemplated may provide for relatively high separation resistance, and also may have relatively high mechanical strength in both the machine direction and cross direction. Also, the aforementioned nonwoven web may exhibit high bulkiness and softness as well as excellent spinnability and excellent anti-flocking property.

Examples of Uses of Fastening System

A fastening system including a landing zone formed of a nonwoven web material including multicomponent fibers as contemplated herein may be incorporated into a variety of consumer and commercial products, which may be provided advantages as a result. In any of the examples described herein, the landing zone may be formed of a patch of separate material, added to the product. For example, the landing zone may be a discrete structure joined to any component (e.g., a topsheet, an absorbent core, a backsheet, a fastening system, a fastening member, a cuff, etc.) of an absorbent article or other commercial good (e.g., a wrap, a medical product, etc.). Alternatively, the landing zone may be constructed as part or all of any element of the commercial good or fastener. For example, the landing zone may be constructed as part or all of any component (e.g., a topsheet, an absorbent core, a fastening member, a backsheet, a fastening system, a cuff, etc.) of an absorbent article or other commercial good (e.g., a wrap, a medical product, etc.). Further, a landing zone may be disposed in any suitable location on or in the commercial good or fastener. For example, the landing zone may be disposed on an outer-facing surface, wearer-facing surface of, or contained within the commercial good or fastener. As another example, an article having a wearer-facing surface and an outer-facing surface may comprise a fastening system as contemplated herein. The fastening system may be disposed on the wearer-facing surface or the outer-facing surface of the article. In some examples, the article may be selected from the group consisting of: an absorbent article, a diaper, a pant, an adult incontinence article, a feminine hygiene article, a body wrap, a bib, and a consumer good. For the sake of explanation, a landing zone as contemplated herein will be discussed, to some extent, in the context of disposable diapers, but such explanation is not intended to limit interpretation of the claims.

As shown in FIGS. 1A and 1B, a disposable absorbent article 600 may comprise a liquid pervious topsheet 622 and a backsheet 624 joined to at least a portion of the topsheet 622. The disposable absorbent article 600 further comprises an absorbent core 646 positioned between the topsheet 622 and the backsheet 624. The disposable absorbent article 600 may further comprise fastening members 628, outer cuffs 632, inner cuffs 652, and waist features 630.

A portion of the periphery of the disposable absorbent article 600 may be defined by the longitudinal edges 675A and 675B; the first waist edge 650, and the second waist edge 651. The longitudinal edges 675A and 675B may run generally parallel to a longitudinal centerline 690 of the disposable absorbent article 600. The first waist edge 650 and the second waist edge 651 may run generally parallel to a lateral centerline 680 of the disposable absorbent article 600. The disposable absorbent article 600 may further comprise elastic leg features 631 which may be disposed adjacent to the longitudinal edges 675A and 675B.

The disposable absorbent article 600 may further comprise a first waist member 602 and a second waist member 604. The first waist member 602 and/or the second waist member 604 may be elastically extensible. As shown, in some examples, the first waist member 602 may be disposed adjacent the first waist edge 650. In some examples, the second waist member 604 may be disposed adjacent to the second waist edge 651. Generally, the first waist member 602 and/or the second waist member 604 may be under tension prior to joining to the disposable absorbent article 600. So, upon release of at least a portion of the tension applied to the first waist member 602 and/or the second waist member 604, a portion of the disposable absorbent article 600 joined thereto can corrugate. This corrugation of the disposable absorbent article 600 can allow the first waist member 602 and/or the second waist member 604 and the disposable absorbent article 600 to expand and contract about the waist of a wearer, thereby providing more comfort and improved fit to a wearer. Examples of suitable waist members 602 and/or 604 include those described in U.S. Pat. No. 4,515,595, U.S. Pat. No. 5,151,092, and U.S. Pat. No. 5,221,274. Although disposable diapers are generally constructed so as to have two elastic waist features, one positioned in a first waist region and one positioned in a second waist region, diapers may be constructed with a single elastic waist feature.

The disposable absorbent article 600 may further comprise outer cuffs 632 and inner cuffs 652 to improve containment of liquids and other body exudates. Each elasticized outer cuff 632 may include several different examples for reducing the leakage of body exudates in the leg regions. Outer cuffs 632 and inner cuffs 652 are further described in U.S. Pat. No. 3,860,003; U.S. Pat. No. 4,909,803; and U.S. Pat. No. 4,695,278.

As stated previously, the disposable absorbent article may further comprise a pair of fastening members 628. As shown in FIG. 1B, the fastening members 628 can extend outward from the first longitudinal edge 675A and the second longitudinal edge 675B of the disposable absorbent article 600. In some examples, the fastening members 628 may be joined to the disposable absorbent article 600 in the second waist region 638, and in some examples, the fastening members 628 may be joined to the disposable absorbent article 600 or in the first waist region 636. Alternatively, in some examples, the disposable absorbent article 600 may comprise a pair of fastening members which are disposed in the second waist region 638 and a pair of fastening members which are disposed in the first waist region 636. In some examples, the fastening members 628 can form a portion of the leg openings when the disposable absorbent article 600 is fastened. The fastening members 628 can form a portion of the leg openings which would be disposed on an outer surface of a leg of a wearer. A crotch region 610 of the disposable absorbent article 600 in conjunction with the first waist region 636 and the second waist region 638 can form a portion of the leg openings which would be disposed on an inner surface of the leg of the wearer. In some examples, the fastening members 628 may be elastically extensible. Fastening members may be formed of an elastically extensible stretch laminate and may also have any of the stress-distributing shape and other features disclosed in, e.g., U.S. Pat. No. 7,870,652, and U.S. application Ser. Nos. 11/638,988; 12/773,181; and 12/904,220 by Kline et al.

The disposable absorbent article 600 further comprises a fastening system 640 which joins at least a portion of a first waist region 636 with at least a portion of a second waist region 638, preferably to form leg and waist openings. The fastening system 640 also works with the waist members(s) 602 and/or 604 to maintain lateral tension in order to keep the disposable absorbent article 600 in place about the waist of the wearer. The fastening system 640 may comprise hooks patches 642 which, in some examples, may be disposed on the fastening members 628. The fastening system 640 may further comprise a landing zone 644 which, in some examples, is disposed in the first waist region 636.

Figure 1C:
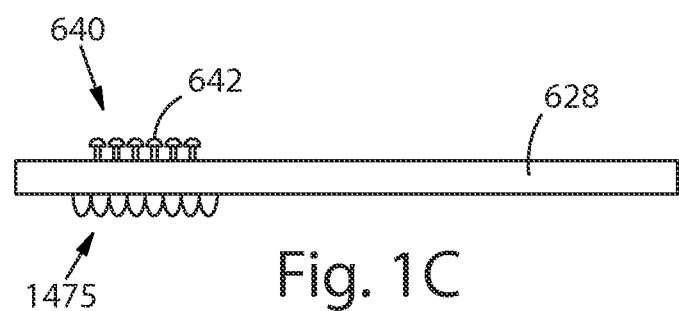
FIG. 1C is an elevation view showing an example of a fastening member that may be included on the disposable absorbent article of FIG. 1A.

As shown in FIG. 1C, in other examples, the fastening system 640 can include a plurality of fastening components on the fastening members 628. For example, as shown, the fastening member 628 may comprise the hooks patch 642 which, in some examples, can include a plurality of engaging elements. Additionally, in some examples, the fastening member 628 may further comprise a landing zone 1475 which is disposed opposite of the hooks patch 642. One advantage of this arrangement is that the hooks patch 642 can engage the landing zone 644 (shown in FIG. 1A) which is joined to the first waist region 636 or can join to the landing zone 1475 of the other fastening member 628.

As shown in FIG. 1A, the landing zone 644 is disposed on the disposable absorbent article 600 such that the overlap of the bond lines 618 is generally perpendicular to the primary direction of shear 775. As shown in FIG. 1A, the primary direction of shear 775 is an expected in use force which typically occurs once the disposable absorbent article 600 is in a fastened state. In some examples, the landing zone 644 may be disposed adjacent the first waist edge 650 in the first waist region 636 on an outer-facing surface of disposable absorbent article 600. In other examples, the landing zone 644 may be disposed adjacent the second waist edge 651 in the second waist region 638. In this example, the hooks patches 642 may be disposed adjacent the first waist region 636. In some examples, landing zones 644 may be disposed on the fastening members 628 and the hooks patch may be disposed in the first waist region 636. In some examples, the landing zone 644 may comprise a plurality of discrete elements.

The landing zone 644 may be formed of, or may include, a section of multicomponent fiber nonwoven web as described herein, which may serve as the receiving or loops component of a hook-and-loop fastening system. At least a portion of the outermost layer of the article may be formed by or include the section of multicomponent fiber nonwoven web. With articles such as diapers, it may be desirable that the section of multicomponent fiber nonwoven web be disposed in at least one of the front or rear waist regions, e.g., as the component forming the outermost layer thereof. In order to provide an area for attachment of hooks, of sufficient size and location to allow for adjustability of fit about the waist, it may be desired that the section of multicomponent fiber nonwoven web be laterally centered and occupy a greater portion of the lateral width of the article, with a bottom edge lying no more than 25 percent of the overall length of the article from the proximate waist edge of the article. It may be preferable that the length of the section of multicomponent fiber nonwoven web serving as landing zone material be from 10 to 20 percent of the overall longitudinal length of the article. In many diaper designs, the location at which fasteners are designed to be attached lies in the front waist region, and thus, it may be desired that the section of multicomponent fiber nonwoven web be disposed in the front waist region (as suggested in FIG. 1A). To provide an effectively large landing zone, it may be desired that the section of multicomponent fiber nonwoven web occupy from 3-10 percent of the total area of the outermost surface of the article.

In another example, however, the entire outermost layer of the article may be formed of the multicomponent fiber nonwoven web. This example may be suitable to provide for attachment of hooks anywhere on the outermost surface of the article that the consumer may desire. For example, in some circumstances, a caregiver may remove a soiled article from a baby and then wish to form it into a closed bundle containing and encapsulating the baby's exudates until the article may be disposed of appropriately. If the entirety of the outermost layer is formed of a multicomponent fiber nonwoven web as described herein, making it suitable for fastenably receiving hooks, the caregiver will be able to quickly and easily position and attach hook-bearing fastening members anywhere on the outer surface, in order to form a closed bundle of the article. In further examples that may be suitable for this purpose, however, a section of multicomponent fiber nonwoven web as described herein may form the outermost layer of a portion of the article that extends along its entire length, but less than its entire width, and may be laterally centered; or the section may form the outermost layer of a portion of the article that extends across its entire width, but less than its entire length.

In the example suggested in FIG. 1C, a section of multicomponent fiber nonwoven web as described herein may form a portion of the outermost or innermost layer of a fastening member 628. This may be desired in circumstances in which the article is desired such that the fastening members may be attached to one another and/or the other portions of the article in an overlapped configuration, either during wear or during storage/transport, or both.

In another example, a section of multicomponent fiber nonwoven web as described herein may form all or a portion of the outermost or innermost layer of a side ear, side panel or side tab of the article, extending laterally from one of the front or rear waist regions. In this position, the section may provide a receiving/attachment component for a cooperating patch of hooks on a cooperating side ear, side panel, side tab or fastening member, such as, for example, in articles having a refastenable pant configuration such as currently marketed PULL-UPS training diapers/pants, a product of Kimberly-Clark Corporation, Neenah, Wis.

A section of multicomponent fiber nonwoven web may also be used to form a nonwoven layer, such as the outermost or innermost layer, of a stretch laminate material used to form side panels, ear panels or fastening members of an article. An example of such stretch laminate material is disclosed in, e.g., U.S. Pat. No. 5,151,092; such use of a stretch laminate is disclosed in, e.g., U.S. Pat. No. 8,016,807.

Examples of Hooks Components

Any suitable hooks component may be used to form a hooks patch 642 may be used for a fastening system as contemplated herein. The hooks patch 642 can mechanically engage fibrous elements of the landing zone 644 so as to provide a secure closure. A hooks patch may be manufactured from a wide range of materials. Suitable materials include nylon, polyester, polypropylene, or any combination of these materials, or other materials as are known in the art.

A suitable hooks component comprises a number of shaped engaging elements projecting from a backing, such as the commercially available material designated SCOTCHMATE brand No. FJ3402 available from Minnesota Mining and Manufacturing Company, St. Paul, Minn. Alternatively, the engaging elements may have any shape such as hooks, "T"-shapes, arrowhead shapes, mushroom shapes, or any other shapes known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some examples, may be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087. Still another suitable hook material that may be desired in some circumstances is the "980" hook material available from Aplix, Inc., Charlotte, N.C. and/or Aplix, Paris France.

Figure 15:
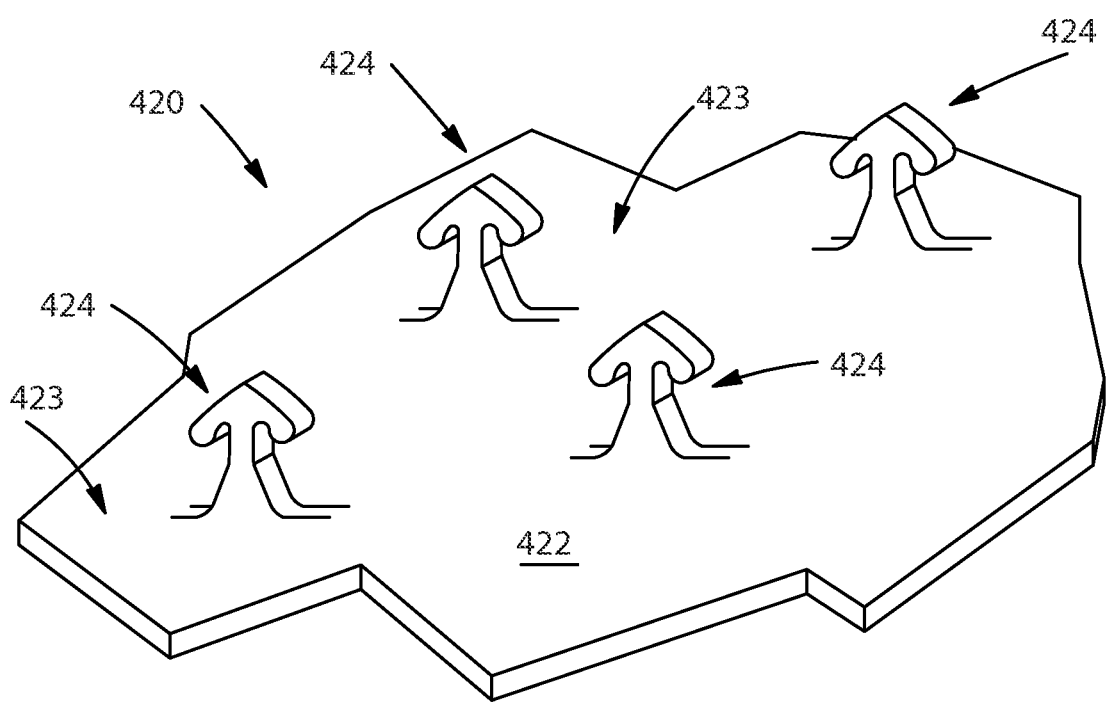
FIG. 15 is an enlarged isometric view of a portion of an example of a hooks patch material.

Further, a fastening system may include any landing zone material described above, with any of the hooks configurations described below. FIG. 15 is an enlarged isometric view of a portion of a hooks patch 642. In FIG. 15, the portion is shown as broken away from a larger piece of material. The hooks patch 642 includes a plurality of bidirectional microsized hooks 424 disposed on a substrate 422 that has an overall planar shape. Each of the hooks 424 may be configured in the same way as the hook 530 of FIGS. 16A-16D, including any alternative examples. Alternatively the hooks patch 642 can also include one or more hooks configured in other ways. In the example of FIG. 15, the hooks 424 and the substrate 422 are made from the same material, and the hooks 424 are a unified part of the substrate 422. The hooks patch 642 may be made from a wide variety of shapeable and/or formable materials, including any of the natural or synthetic materials recited herein and/or any other suitable material suitable known in the art, in any workable combination, along with any additives or processing aids known in the art. As a particular example, the hooks patch 642 may be made from various renewable materials, including bioplastics derived from renewable biomass sources such as sugars, starches, cellulose, biopolymers, etc. In various alternate examples, the hooks and the substrate may be formed separately, or made from different materials.

The hooks 424 may be distributed across the hooks patch 642 in various patterns and hook densities. For example, the hooks 424 may be arranged in rows and/or columns, or any other arrangement of hooks known in the art. In various examples, the hooks patch material may have a hook density of 10-1,000 hooks per square centimeter, or any integer number of hooks between 10 and 1,000, or any range formed by any of these values.

Following are examples of hooks patch materials suitable for use in a hook and loop fastening system. A hooks patch material can include hooks having any shape such as a "J" shape, a "T" shape, or a mushroom shape, or any other shape known in the art. Exemplary hooks patch materials are available from Aplix, Inc. of Charlotte, N.C., USA under the trade designation 960, 957, and 942. Other hooks patch materials are available from the 3M Company of St. Paul, Minn., USA under the trade designations CS200, CS300, MCS, and MC6. Still other hooks patch materials are described in U.S. Pat. No. 5,058,247 entitled "Mechanical Fastening Prong" issued to Thomas Oct. 22, 1991, which is hereby incorporated by reference.

The hooks patch 642 and the hooks 424 thereon may be made by any suitable process known in the art. For example, the hooks patch material may be made by casting, molding, profile extrusion, or microreplication. Further, the hooks patch material may be made by using any process described in any of the following U.S. Pat. Nos. 3,192,589; 3,138,841; 3,266,113; 3,408,705; 3,557,413; 3,594,863; 3,594,865; 3,718,725; 3,762,000; 4,001,366; 4,056,593; 4,189,809: 4,290,174; 4,454,183; 4,894,060; 5,077,870; 5,315,740; 5,607,635; 5,679,302; 5,879,604; 5,845,375; 6,054,091; 6,206,679; 6,209,177; 6,248,419; 6,357,088; 6,481,063; 6,484,371; 6,526,633; 6,635,212; 6,660,202; 6,728,998; 6,737,147; 6,869,554; RE38,652; 6,982,055; 7,014,906; 7,048,818; 7,032,278; 7,052,636; 7,052,638; 7,067,185; 7,172,008; 7,182,992; 7,185,401; 7,188,396; and 7,516,524, each of which is hereby incorporated by reference.

In another alternate example, the hooks may be joined together to form a hooks patch material without a substrate that has an overall planar shape. For example, a hooks patch material may be made from a plurality of hooks that are disposed on one or more strips of material, or disposed on one or more strands of material, or hooks that are joined together to form one or more strips or one or more strands of material, or hooks that are connected to one or more other common elements, in any manner known in the art.

FIG. 16A is an enlarged view of a front 532 of a bidirectional micro-sized hook 530 disposed on a top surface 523 of a portion of a substrate 522 of a hooks patch material. In FIG. 16A, the portion of the substrate 522 is shown as broken away from a larger piece of material. The hook 530 is bidirectional since the cap 570 has two arms 580, extending from opposite sides 536 of the hook 530. The sides 536 of the hook are the outside portions of the hook 530, between a front 532 of the hook 530 and a back 534 of the hook 530. While the hook 530 is a bidirectional hook, it is contemplated that any of the structures, features, sizes, or dimensions of the hook 530 may be similarly applied to a unidirectional hook (one arm configured to hook in one direction) or to a multi-directional hook (more than two arms, with each arm configured to hook in a different direction).

In the example of FIG. 16A, both of the arms 580 of the hook 530 are configured in the same way. However, it is also contemplated that any of the structures, features, sizes, or dimensions of an arm 580 of the hook 530 may be applied to one arm of a bidirectional hook, while the other arm may be configured in a different way. Further, it is contemplated that any of the structures, features, sizes, or dimensions of an arm 580 of the hook 530 may be applied to two or more arms of a multi-directional hook, while one or more other arms on that hook may be configured in one or more different ways.

The hook 530 includes a base 550, a stem 560, and a cap 570. The hook 530 also has sides 536. The hook 530 projects out from the substrate 522 in an upward direction 545, which is perpendicular to the substrate 522. The hook 530 also has a width direction 547. The width direction 547 is parallel to the overall planar shape of the substrate 522 and parallel to the largest linear dimension measured across the cap 570. In the example of FIG. 16A, the width direction 547 is also parallel to the front 532 of the hook 530 and perpendicular to the sides 536. The hook 530 also has a thickness direction 541, which is parallel to the substrate 522 and perpendicular to the width direction 547. The thickness direction 541 is perpendicular to the page in FIG. 16A, so the thickness direction 541 is shown in FIGS. 16B and 16C.

Figure 16D:
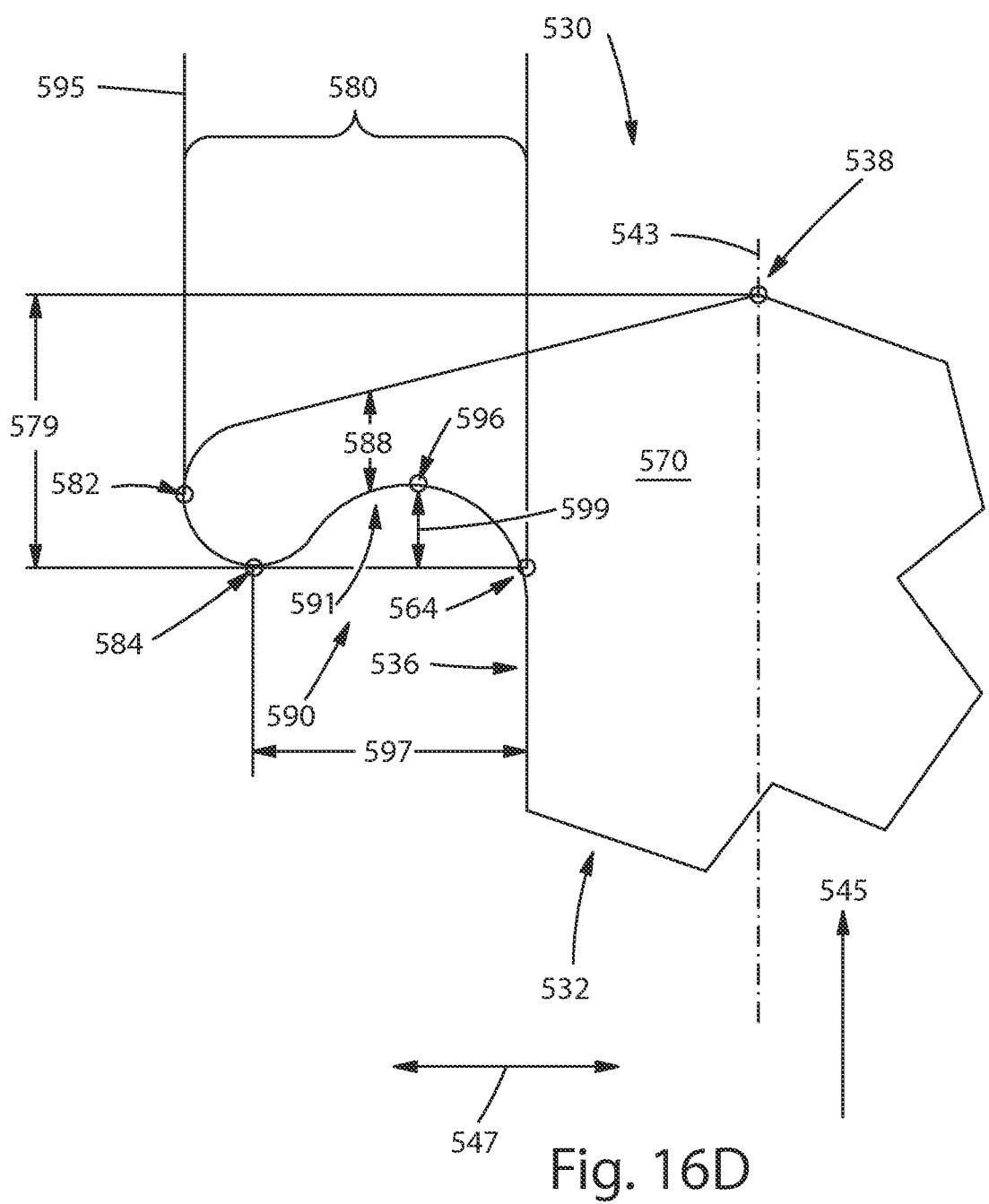
FIG. 16D is a further enlarged view of a portion of a front of the hook of FIG. 16A.

The base 550 is attached to the substrate 522, the stem 560 is attached to the base 550, and the cap 570 is attached to the stem 560. The cap 570 has an overall cap height 579, which is measured as described in connection with FIG. 16D. The hook 530 also has an overall hook height 539 measured linearly in the upward direction 545 from the top surface 523 of the substrate 522 to a highest point on the outer surface of the hook 530 (farthest away from the top surface 523 of the substrate 522). In the example of FIG. 16A, a peak 538 of the cap 570 is the highest point on the outer surface of the hook 530. The hook 530 also has a central axis 543, which passes through the center of the hook. In the example of FIG. 16A, the central axis 543 is aligned with the upward direction 545, however, in various examples, the central axis 543 may not be perpendicular with respect to the substrate 522; that is the hook may be tipped in the width direction 547 and/or the thickness direction 541. Also, in various examples the cap 570 may not have a peak, but may have a rounded top, or a flat top, or a recessed top, or any other shape known in the art or combinations of any of these.

When the hook 530 is used on a hooks patch material of a fastening system, and the fastening system uses a fibrous material as the landing zone material, the overall hook height 539 may be sized to the overall thickness of the fibrous material, such as the overall thickness of the landing zone material. The overall hook height 539 may be 33-200% of the overall thickness of the fibrous material, or any integer value of percentage between 33% and 200% of the overall thickness of the fibrous material, or any range formed by any of these values. As examples, the overall hook height 539 may be 33%, 50%, 100%, 150%, or 200% of the overall thickness of the fibrous material, or any range formed by any of these values. While not wishing to be bound by this theory, it is believed that, selecting an overall hook height 539 based on the overall thickness of the fibrous material, as described above, allows the hook 530 to penetrate the fibrous material to a significant depth, which increases the likelihood that the hook 530 can encounter fibers to be captured by the hook 530.

FIG. 16B is an enlarged side view of the hook 530 of FIG. 16A disposed on the top surface 523 of a portion of the substrate 522. In FIG. 16B, the portion of the substrate 522 is shown as broken away from a larger piece of material. The hook 530 has the front 532 and the back 534, each of which is substantially flat, however in various examples the front 532 and/or the back 534 may not be flat. FIG. 16B illustrates the thickness direction 541, which is parallel to the substrate 522 and perpendicular to the width direction 547. In the example of FIG. 16A, the thickness direction 541 is also perpendicular to the front 532 and the back 534 of the hook 530.

FIG. 16C is an enlarged top view of the hook of FIG. 16A. The top view of the hook 530 shows a top view of the cap 570. The cap 570 has a front edge 572, a back edge 574, and side edges 576. In the example of FIG. 16A, each of these edges is substantially flat, however in various examples any of these edges may not be flat. For example, any of the edges of the cap 570 may be curved inward or outward to form a concave or convex shape, or may have other variations in its geometry. The front edge 572 and the back edge 574 are parallel with the width direction 547 and with each other, however in various examples these edges may not be parallel. The side edges 576 are parallel with the thickness direction 541 and with each other, however in various examples these edges may not be parallel. The front edge 572 and the back edge 574 have the same overall width 557, which is measured linearly in the width direction 547, however in various examples the overall widths of the front and back edges may differ. The side edges 576 have the same overall thickness 578, which is measured linearly in the thickness direction 541, however in various examples the overall widths of the side edges may differ.

The front edge 572, the back edge 574, and the side edges 576 together, when viewed from above the peak 538 of the hook 530, define a vertical effective engagement area 577. That is, the vertical effective engagement area 577 is an area measured in a plane that is parallel with the substrate 522 and above the highest point of the hook 530, wherein the area is defined by the perimeter of the cap 570. In the example of FIG. 16C, the perimeter of the cap 570 is formed by the front edge 572, the back edge 574, and the side edges 576, so these edges define the vertical effective engagement area 577. In the example of FIG. 16C, the vertical effective engagement area 577 has an overall shape that is rectangular, however, in various examples, the overall shape may vary, based on the size and shape of the edges.

The vertical effective engagement area 577 has a width-to-thickness aspect ratio, which is defined as the widest overall width of the vertical effective engagement area 577 divided by the thickest overall thickness of the vertical effective engagement area 577. The width-to-thickness aspect ratio may be 1-2, or any value in increments of 0.01 between 1 and 2, or any range formed by any of these values. As examples, the width-to-thickness aspect ratio may be 1.2, 1.3, 1.6, 1.8, or 1.9, or any range formed by any of these values. In the example of FIG. 16C, the vertical effective engagement area 577 has a width-to-thickness aspect ratio, which is the overall width 557 divided by the overall thickness 578. While not wishing to be bound by this theory, it is believed that, selecting these aspect ratios for the vertical effective engagement area 577, as described above, provides the cap 570 of the hook 530 with an overall shape that is less elongated so as to more easily fit into openings (between fibers) in the fibrous material, which increases the likelihood that the hook 530 can penetrate the fibrous material.

The size of the vertical effective engagement area 577 may be 40,000-120,000 square micrometers, or any value in increments of 5,000 square micrometers between 40,000 and 120,000 square micrometers, or any range formed by any of these values. As examples, the vertical effective engagement area 577 may be 40,000, 50,000, 60,000, 90,000, 100,000, or 120,000 square micrometers, or any range formed by any of these values. While not wishing to be bound by this theory, it is believed that, selecting these area dimensions for the vertical effective engagement area 577, as described above, provides the cap 570 of the hook 530 with an overall size that is small enough to easily fit into openings (between fibers) in the fibrous material, which increases the likelihood that the hook 530 can penetrate the fibrous material.

FIG. 16D is a further enlarged view of a portion of the front 532 of the hook 530 of FIG. 16A. In FIG. 16D, the portion is shown as broken away from the rest of the hook 530. FIG. 16D shows a portion of the cap 570. The portion of the cap 570 shown in FIG. 16D includes the arm 580, which extends outward from the side 536.

The structures and dimensions of the arm 580 are defined with respect to several points of reference. One reference point is a farthest point 582 on the arm 580. The farthest point 582 is a point on the arm 580 that is farthest outward from the side 536 of the hook. In FIG. 16D, the farthest point 582 is also the point on the side edge 576 of the cap 570 that is farthest away from the central axis 543. Another reference point is a lowest point 584 on an outboard end of the arm 580. The lowest point 584 is a point on the outboard end of the arm 580 (the portion of the arm 580 that is not disposed near the side 536) that is closest to the top surface 523 of the substrate 522. Still another reference point is the side point 564. The side point 564 is a point on the side 536 of the hook 530. The specific location of the side point 564 is defined by a reference plane that is parallel to the substrate 522. The reference plane passes through the lowest point 584 on the arm 580. The side point 564 is a point in the reference plane and on the side 536 of the hook that is closest to the lowest point 584.

The arm 580 begins at the side point 564. The portion of the hook 530 that is attached above the side point 564 and that is disposed outboard from the side point 564 is defined as the arm 580. The arm 580 extends from the side 536, in the width direction 547, to the farthest point 582 on the arm 580. If a hook does not include a portion that is attached above a side point and that is disposed outboard from a side point, then, for purposes of the present disclosure, the hook does not include an arm.

The cap 570 has an overall cap height 579 measured linearly in the upward direction 545 from the lowest point 584 to the highest height of the cap 570, which is the peak 538 of the cap 570 in FIG. 16D.

When the hook 530 is used on a hooks patch material of a fastening system, and the fastening system uses a fibrous material as the landing zone material, the overall cap height 579 may be sized to the average thickness of the fibrous material, such as the average thickness of the landing zone material. The overall cap height 579 may be 1-33% of the average thickness of the fibrous material, or any integer value of percentage between 1% and 33% of the average thickness of the fibrous material, or any range formed by any of these values. As examples, the overall cap height 579 may be less than or equal to 20% or less than or equal to 25% of the average thickness of the fibrous material. While not wishing to be bound by this theory, it is believed that, selecting these relative dimensions for the overall cap height 579, as described above, provides the cap 570 of the hook 530 with an overall size that is short enough such that there is a large open space between the lowest point 584 on the arm 580 and the top surface 523 of the substrate 522, which allows relatively more fibers to fit under the arm 580 and increases the likelihood that fibers will be captured by the hook 530.

Also, the overall cap height 579 may be sized to the average fiber cross-sectional dimension of the fibrous material, such as the average cross-sectional dimension of the fibers of the landing zone material. The overall cap height 579 may be 1-8 times the average fiber cross-sectional dimension, or any integer value between 1 and 8 times the average fiber cross-sectional dimension, or any range formed by any of these values. As examples, the overall cap height 579 may be less than or equal to 6 times or less than or equal to 7 times the average fiber cross-sectional dimension. While not wishing to be bound by this theory, it is believed that, selecting these relative dimensions for the overall cap height 579, as described above, provides the cap 570 of the hook 530 with an overall size that is short enough such that the side of the cap 570 is less likely to interfere with fibers, as the hook 530 moves through the fibrous material.

Further, the overall cap height 579 may be sized to a particular dimension. The overall cap height 579 may be 5-120 micrometers, or any value in increments of 5 micrometers between 5 and 120 micrometers, or any range formed by any of these values. As examples, the overall cap height 579 may be less than or equal to 80 micrometers or less than or equal to 100 micrometers. While not wishing to be bound by this theory, it is believed that, selecting these particular dimensions for the overall cap height 579, as described above, provides the cap 570 of the hook 530 with an overall size that is short enough such that there is a large open space between the lowest point 584 on the arm 580 and the top surface 523 of the substrate 522, which allows relatively more fibers to fit under the arm 580 and increases the likelihood that fibers will be captured by the hook 530.

The arm 580 has an underside 590, which is the bottom part of the arm 580 that is facing somewhat downward, toward the top surface 523 of the substrate 522. In various examples, an arm of a hook may or may not include a recessed portion. If the outer surface of the underside of an arm includes a point that is farther away from the top surface of the substrate than the lowest point on the arm, then the arm includes a recessed portion. In the example of FIG. 16A, since the underside 590 of the arm 580 includes a number of points that are farther away from the top surface 523 of the substrate 522 than the lowest point 584 on the arm 580, the arm 580 includes a recessed portion 591.

If the outer surface of the underside of an arm does not include a point that is farther away from the top surface of the substrate than the lowest point on the arm, then the arm does not include a recessed portion. For example, a hook can include an arm with an underside that is parallel to the top surface of the substrate to which the hook is attached. In this example, the hook includes an arm, but the arm does not include a recessed portion.

The recessed portion 591 has an overall recessed width 597 measured linearly in the width direction 547 from the lowest point 584 on the arm 580 (as described above) to the side point 564. When the hook 530 is used on a hooks patch material of a fastening system, and the fastening system uses a fibrous material as the landing zone material, the overall recessed width 597 may be sized to the average cross-sectional dimension of the fibrous material, such as the average fiber cross-sectional dimension of the fibers of the landing zone material. The overall recessed width 597 may be 200-500% of the overall fiber cross-sectional dimension, or any integer value of percentage between 200% and 500% of the overall fiber cross-sectional dimension, or any range formed by any of these values. As examples, the overall recessed width 597 may be 200%, 300%, 400%, or 500% of the overall fiber cross-sectional dimension, or any range formed by any of these values. While not wishing to be bound by this theory, it is believed that, selecting these relative dimensions for the overall recessed width 597, as described above, allow two to five fibers to fit in the recessed portion 591, which increases the likelihood that fibers may be retained by the hook 530.

The recessed portion 591 has a deepest recessed depth 599 measured linearly in the upward direction 545 from the lowest point 584 on the arm 580 (as described above) to the deepest point 596 on the underside 590 of the arm 580. The deepest point 596 is the point on the outer surface of the underside 590 of the arm 580, between the lowest point 584 and the side point 564, which is farthest from the top surface 523 of the substrate 522. In the example of FIG. 16D, the recessed portion 591 is smooth and continuously curved. However, in various examples a recessed portion may have a surface that is flat, or rough, or irregular, or curved with curves separated by one or more discontinuities.

When the hook 530 is used on a hooks patch material of a fastening system, and the fastening system uses a fibrous material as the landing zone material, the deepest recessed depth 599 may be sized to the average cross-sectional dimension of the fibers of the fibrous material, such as the average cross-sectional dimension of the fibers of the landing zone material. The deepest recessed depth 599 may be 40-200% of the overall fiber cross-sectional dimension, or any integer value of percentage between 40% and 200% of the overall fiber cross-sectional dimension, or any range formed by any of these values. As examples, the deepest recessed depth 599 may be 50%, 60%, 100%, or 150% of the overall fiber cross-sectional dimension, or any range formed by any of these values. While not wishing to be bound by this theory, it is believed that, selecting these relative dimensions for the deepest recessed depth 599, as described above, allows one or more fibers to fit in the recessed portion 591, and increases the likelihood that fibers will be retained by the hook 530.

The deepest recessed depth 599 can also be sized in relation to the overall cap height 579. The deepest recessed depth 599 may be 10-60% of the overall cap height 579, or any integer value of percentage between 10% and 50% of the overall cap height 579, or any range formed by any of these values. As examples, the deepest recessed depth 599 may be 10%, 20%, 50%, or 60% of the overall cap height 579, or any range formed by any of these values.

The arm 580 has a thinnest arm portion 588, when measured (in the portion of the arm that corresponds with the recessed portion 591) linearly in the upward direction 545. When the hook 530 is used on a hooks patch material of a fastening system, and the fastening system uses a fibrous material as the landing zone material, the thinnest arm portion 588 may be sized to the average cross-sectional dimension of the fibers of the fibrous material, such as the average cross-sectional dimension of the fibers of the landing zone material. The thinnest arm portion 588 may be 70-760% of the average fiber cross-sectional dimension, or any integer value of percentage between 70% and 760% of the average fiber cross-sectional dimension, or any range formed by any of these values. As examples, the thinnest arm portion 588 may be 100%, 150%, 500%, or 760% of the average fiber cross-sectional dimension, or any range formed by any of these values.

FIG. 17 is an enlarged view of a front 832 of another bidirectional micro-sized hook 830 disposed on a top surface 823 of a substrate 822 of a hooks patch material. The elements of the hook 830 are configured in the same way as the like-numbered elements of the hook 530 of FIGS. 16A-16D, except as otherwise described below. The hook 830 includes a base 850 that, when followed upward 845 from the top surface 823 of the substrate 822, narrows then widens then narrows again, up to a stem 860. The undersides 890 of arms 880 have recessed portions 891. Each recessed portion 891 is flat and angled outward from the stem 860 at point 893. The recessed portion 891 also includes a discontinuity 894 that separates the flat portion from a curve near the outboard end of the arm 880. The cap 870 of the hook 830 has a top with a recess 875. As a result, the highest point on the outer surface of the hook 830 is not a peak disposed at central axis 843, but is a point 837 at an edge of the recess 875. Part, parts, or all of the hook 830 can also be configured according to any of the alternative examples disclosed for the hook 530 of FIGS. 16A-16D.

Arrangement of Fastening System on Exemplary Article

The fastening system 640 may be the primary fastening system for joining the first and second waist regions 636 and 638. However, the fastening system 640 may be used alone or in conjunction with other fastening means such as tab and slot fasteners, tape fasteners, snaps, buttons, and the like to provide different fastening characteristics. For example, the fastening system 640 may provide the disposable absorbent article 600 with a disposal means for fastening the disposable absorbent article 600 in a configuration convenient for disposal. Further, secondary fastening means may provide the disposable absorbent article 600 with a means for adjusting fit or may increase the strength of the connection between the first waist region 636 and the second waist region 638.

Figure 14A:
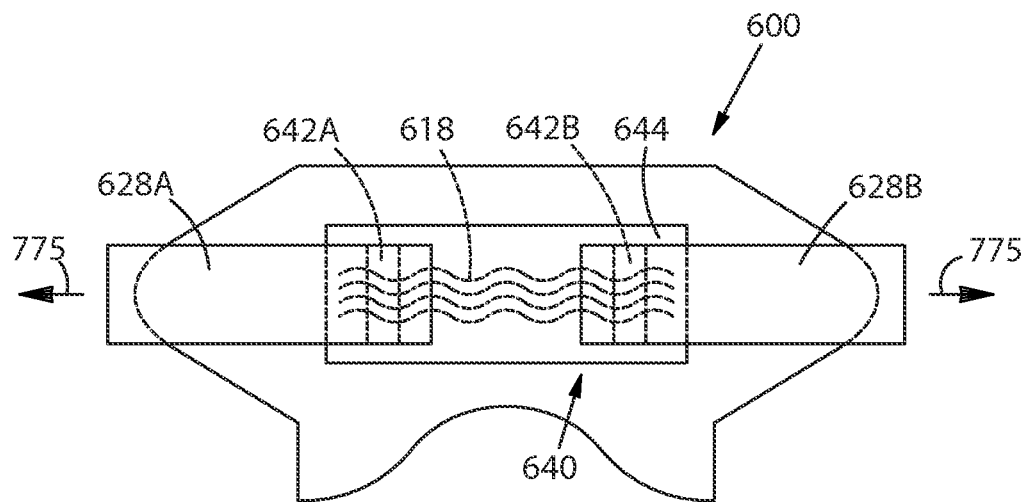
FIG. 14A is an elevation view showing a portion of a wearable article with a fastening system in a fastened state.
Figure 14B:
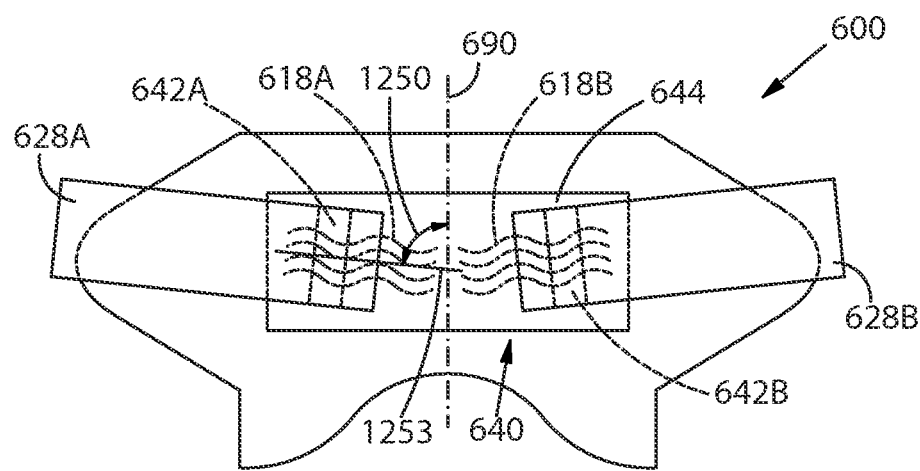
FIG. 14B is an elevation view showing a portion of a wearable absorbent article with a fastening system in a fastened state, wherein a landing zone of the fastening system is disposed on the article to provide a visual alignment aid.

The fastening system 640 may be prefastened in a package such that a caregiver or wearer may pull on the disposable absorbent article 600 when removed from the package. Alternatively, the fastening system 640 may be unfastened in the package such that the caregiver or wearer fastens the fastening system 640 while donning the disposable absorbent article 600. In yet another example, a package may comprise both prefastened and unfastened disposable absorbent articles 600 for the convenience of the caregiver or the wearer. As shown in FIG. 14A, a portion of a disposable absorbent article 600 comprising a fastening system 640 is shown. The fastening system 640 comprises a first hooks patch 642A disposed on a first fastening member 628A and a second hooks patch 642B disposed on a second fastening member 628B. The first hooks patch 642A and the second hooks patch 642B can engage the landing zone 644 when fastened.

The landing zone 644 may comprise a plurality of bond lines 618. Each of the plurality of bond lines 618 may comprise hills and valleys. As mentioned previously, the landing zone 644 may be disposed on the disposable absorbent article 600 such that the overlap between the bond lines is generally perpendicular to the primary direction of shear 775. So, landing zones constructed with features similar to the landing zone (shown in FIGS. 2A-11) may be disposed on the disposable absorbent article 600 such that the cross direction of the landing zone is generally parallel to the primary direction of shear 775.

Examples of Other Article Features

Disposable absorbent articles may comprise many components, elements, members, etc. and may be constructed in a variety of manners. For example, the topsheet 622 (shown in FIG. 1B) and the backsheet 624 (shown in FIG. 1B) may have length and width dimensions generally larger than those of the absorbent core 626 (shown in FIG. 1B). The topsheet 622 (shown in FIG. 1B) and the backsheet 624 (shown in FIG. 1B) can extend beyond the edges of the absorbent core 626 (shown in FIG. 1B), thereby forming the periphery of the disposable absorbent article 600 (shown in FIG. 1B). The topsheet 622 (shown in FIG. 1B), the backsheet 624 (shown in FIG. 1B), and the absorbent core 626 (shown in FIG. 1B) may include many different materials and may be assembled in a variety of well known configurations, exemplary diaper materials and configurations are described generally in U.S. Pat. No. 3,860,003, U.S. Pat. No. 5,151,092, and U.S. Pat. No. 5,221,274.

In addition to serving as the material from which a discrete patch of landing zone material may be cut for affixation to a disposable absorbent article (such as a diaper), the multicomponent fiber webs and/or multilayer webs with multicomponent fiber layers described herein may be used as the outer layer component of a multilayer backsheet. Many current disposable diapers have a backsheet formed, for example, of a laminate of a polymer film layer and an outer layer of nonwoven web. The polymer film selected may be effectively liquid impermeable under the conditions in which diapers are used by consumers, and may be included for containment of liquid exudates, while the outer layer of nonwoven web may be included to impart a soft, cloth-like feel and appearance to the backsheet. It is contemplated that the nonwoven webs with multicomponent fiber components described herein may serve not only as landing zone material, but also as the outer nonwoven web layer of a disposable diaper backsheet. In some circumstances, use of a nonwoven web formed at least in part of multicomponent fibers as described herein, to form the outer nonwoven web layer of a backsheet, may enable the manufacturer to dispense with a separate, discrete landing zone material altogether and the processes needed to apply such material to the article. As described herein, a nonwoven web formed at least in part of multicomponent fibers may not only have the tactile softness and visual appearance desired to impart cloth-like attributes to a backsheet (with tactile softness and apparent loft enhanced by the crimp of the multicomponent fibers forming the nonwoven web), but may also provide a suitable (i.e., providing for suitable separation resistance) substrate for attachment of hooks at any location desired by the consumer, providing increased flexibility in the manner in which the product may be designed for fastening.

Test/Measurement Methods

Separation Resistance

A constant rate of extension tensile tester with computer interface (such as a MTS SYNERGIE 200 tensile tester, controlled with TestWorks 4 software, as available from MTS Systems Corp., Eden Prairie, Minn., or equivalent), fitted with an appropriate load cell is used for this test. The load cell should be selected to be operated within 10% and 90% of its stated maximum load.

All testing is performed in a conditioned room maintained at about 23° C.±2 C.° and about 50%±2% relative humidity.

Precondition the samples at about 23° C.±2 C.° and about 50%±2% relative humidity for 2 hours prior to testing.

For this test, two custom fixtures are fabricated. Referring to FIG. 20A the upper fixture 50 includes a rectangular foot 51 that attaches to the upper movable crosshead of the tensile tester and has a downward-facing planar surface 52 orthogonal to the path of travel of the cross head, onto which a hooks material specimen is to be affixed. The lower fixture 60 attaches to the bottom, stationary mount of the tensile tester, and consists of a support shaft 61, upper support plate 62 and a ball bearing slide mechanism 64 having affixed thereto a mounting plate 65 having an upward-facing planar surface 66 orthogonal to the path of travel of the crosshead, onto which the nonwoven material specimen is to be affixed. Thus, when the test is performed, the "loops" side of the nonwoven material specimen is oriented facing, and parallel to, the hooks side of the hooks material specimen, as they would be oriented on a wearable article on which the materials are used as components of a fastening system.

Still referring to FIG. 20A, the upper fixture 50 consists of a rectangular foot 51 affixed to a suitable mounting device such as an upper mounting shaft 53 adapted to connect to the movable crosshead of the tensile tester. Upper mounting shaft 53 is threaded as shown, and has a locking collar 54. When the upper mounting shaft 53 is connected to the mount of the crosshead, the locking collar 54 is turned against the mount, to immobilize the fixture 50 relative the crosshead, such that it will move integrally along with the crosshead during testing, without interplay therebetween. The foot 51 is formed of aluminum with a downward-facing, planar, brushed-finish surface 52 orthogonal to the path of travel of the crosshead. The downward-facing surface 52 must be of sufficient length and width to accept the entirety of a hooks specimen sized as specified below. The shorter side extends in a left-right direction, and must be substantially centered about the axis of upper mounting shaft 53. The top edge of the foot 51 forms a "T" in the left-right direction, to aid the analyst while mounting the hooks material specimen.

Figure 20B:
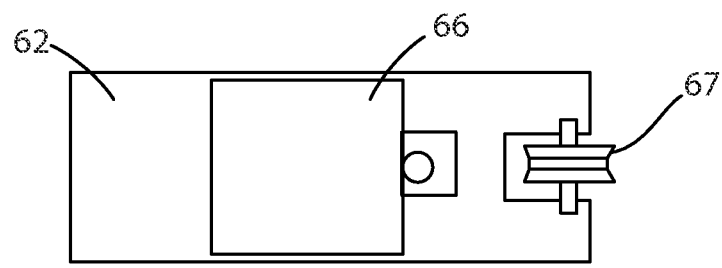
FIG. 20B is a schematic top view of some of certain components of a fixture used to perform the Separation Resistance test described herein.
Figure 20A:
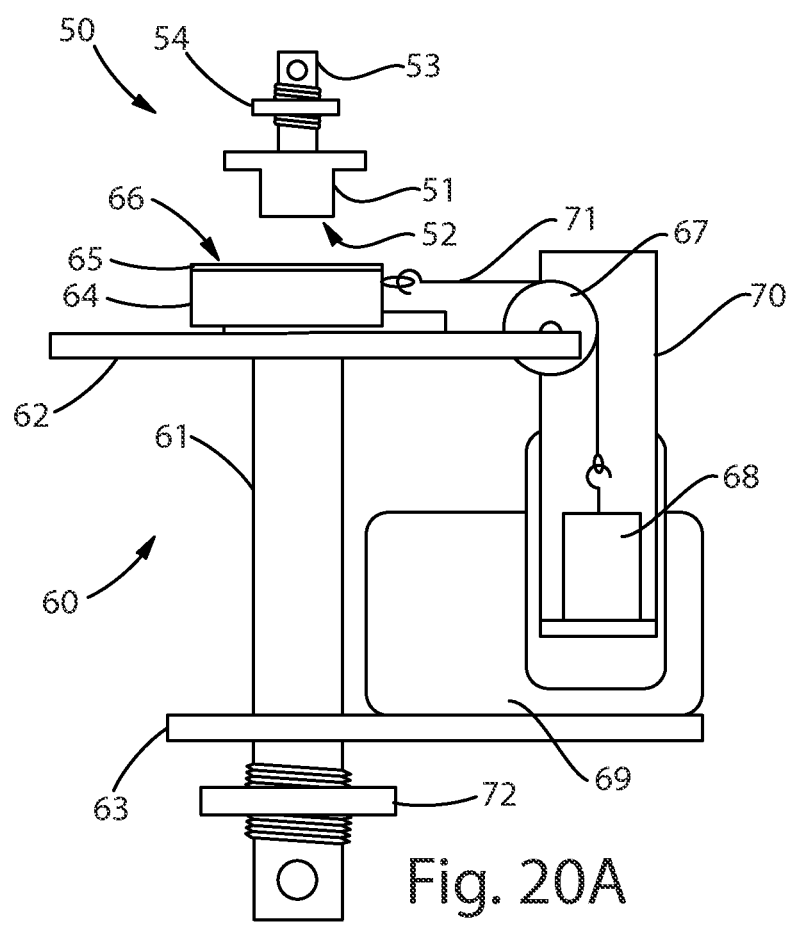
FIG. 20A is a schematic front view of certain components of a fixture used to perform the Separation Resistance test described herein.

Referring to FIGS. 20A and 20B, the lower fixture 60 consists of a support shaft 61 with two horizontal support plates 62 and 63. The lower end of the support shaft 61 is designed to fit within the bottom mount of the tensile tester and is threaded as shown. When the support shaft 61 is connected to the base of the tensile tester, a locking collar 72 is turned against the mount, to immobilize lower fixture 60 and align it vertically with the upper fixture 50. Ball bearing slide mechanism 64 (McMaster Carr, Robbinsville, N.J., Part No. 6257K28 or equivalent) is mounted on the upper support plate 62 such that when the slide mechanism 64 is at its left-most position, mounting plate 65 is centered under the upper fixture 50. The slide mechanism is configured and oriented to allow horizontal, substantially unrestricted left-right movement of mounting plate 65 with no substantial vertical, or other horizontal, play. Mounting plate 65 is affixed to slide mechanism 64, with an upward-facing, planar, brushed-finished surface 66, orthogonal to the path of travel of the crosshead. The upward-facing surface 66 must be of sufficient length and width to accept the entirety of a nonwoven material specimen sized as specified below. The downward-facing surface 52 and the upward-facing surface 66 of the two fixtures are parallel with a parallelism tolerance of no more than 0.01 mm. The right end of the upper support plate 62 is forked to accommodate a low-friction pulley 67 (see FIG. 20B). The pulley 67 translates a vertical force from a suspended shear force weight 68 to a horizontal force applied to the slide mechanism 64 via a flexible non-elastic wire or cable 71 that is connected to the slide mechanism, threaded overtop the pulley and attached to the weight. (For purposes hereof, "non-elastic wire or cable" means that the wire or cable does not elongate more than 3 mm per 150 mm under a load of 7 N.) The shear force weight 68 is removable so that differing selected shear force weights can be used in the test, depending on the desired shear force. The shear force weight 68 rests on a movable platform 70 that is raised and lowered vertically (see FIGS. 20C and 20D) by a linear actuator 69 (McMaster-Carr, Part No. 2236K4 or equivalent) calibrated to move at 2.3 to 2.6 mm/sec. The configuration is such that the movable platform 70 in the uppermost position (e.g. FIG. 20C) supports the weight 68 so that it applies substantially no shear force to the slide mechanism (i.e., there is slack in the wire 71), and in the downwardmost position (e.g. FIG. 20D) allows the weight 68 to hang freely for the remaining duration of the test until after the hooks disengage from the loops.

If either or both of the respective nonwoven material and hooks material to be tested are separate, and not present as components of a wearable article, obtain respective samples of them of sizes sufficient to yield specimens of sizes and orientations indicated in the instructions below, with orientations with respect to machine direction and hooks orientation in accordance with the orientations in which the materials would appear if used as components of a fastening system on a wearable article.

If either or both of the respective nonwoven material and hooks material to be tested exist as components of a fastening system on a wearable article, samples of the materials must be removed from the article to prepare the test specimens as described below.

For the nonwoven material, identify the landing zone portion of the article. Carefully remove the nonwoven material forming the landing zone from the underlying outer cover or backsheet of the article, using cryogen freeze spray (such as CytoFreeze, Control Company, TX) as necessary to deactivate any adhesives. If the article does not have a distinct landing zone, or the nonwoven material forming the landing zone cannot be removed from an underlying layer(s) without causing damage, sever a sample of the nonwoven material and underlying layer(s) from the landing zone region, and remove underlying loose materials from the back side, to the extent possible.

Place the nonwoven material sample on a bench with the outward-facing nonwoven ("loop") side facing downward and the top edge (i.e., the edge which was closest to the front waist edge while on the article) farthest from you. With a permanent fine marker such as a SHARPIE and a straightedge, draw a line on the sample corresponding to the longitudinal midline of the article. Write the letter "R" several times backward (i.e., inverted left to right) across the right side of the nonwoven material sample (as it appeared on the article, "right" and "left" according to the positions of the material on the article as the article would be worn, with respect to the intended wearer's right and left sides). Write the letter "L" several times backward across the left side of the nonwoven material sample. Prepare a tape laminate to be used to attach the loops to the upward-facing surface 66, by attaching a layer of 3M 1524 Transfer Adhesive to a strip of 3M Double Coated Tape 9589. Remove the backing paper of the 3M 1524 and carefully without forming wrinkles or bubbles, attach the nonwoven material sample, "loop" side up, to the 3M 1524/9589 laminate. The nonwoven material sample/tape laminate is them cut to form a rectangular nonwoven material specimen of dimensions approximately 51 mm measured along the article's longitudinal direction, and 26 mm measured along the article's lateral direction.

Smaller nonwoven material specimens may be used, however, provided directional orientations reflecting those of the materials as they appeared on the article for use as fastening components are observed, and the nonwoven material specimen dimensions are larger than the hooks material specimen described below. The edges of the tape of the specimen should extend to, but not past, the edges of the nonwoven material. If any tape adhesive or other adhesive is exposed on the specimen, deactivate it with talcum powder, starch powder or other appropriate material.

For the hooks material, carefully remove the hooks material from the article using cryogen freeze spray as necessary to deactivate any adhesives. If the hooks material cannot be removed without damage, sever the material upon which the hooks material is affixed from the article and remove all loose materials from the reverse side. Prepare a tape laminate to be used to attach the hooks material sample to the downward-facing surface 52 of the upper fixture 50, by attaching a layer of 3M 1524 Transfer Adhesive to a strip of 3M Double Coated Tape 9589. Remove the backing tape of the 3M 1524, and carefully, without forming wrinkles or bubbles, attach the hooks material sample, hooks up, to the 3M 1524/9589 laminate. The hooks material/tape laminate is then cut to form a rectangular hooks material specimen 13 mm±0.05 mm measured along the direction corresponding to the article's lateral direction and 25.4 mm±0.05 mm measured along the direction corresponding to the article's longitudinal direction. The edges of the tape of the specimen should extend to, but not past, the edges of the hooks material. If any tape adhesive or other adhesive is exposed on the specimen, deactivate it with talcum powder, starch powder or other appropriate material.

Remove the backing paper from the tape side of the prepared nonwoven material specimen and place it, "loops" side up, onto the upward-facing surface 66, such that the lateral direction (with respect to the article from which the specimen was taken) is oriented left-to-right. Gently place a 250 g weighted plate (surface of 50 mm×76 mm) onto the nonwoven material specimen. Without applying any additional pressure, slide the plate over the entire surface of nonwoven material specimen, to adhere it to upward-facing surface 66.

Nonwoven material specimens prepared from both the right and left sides of the landing zone are to be tested. The nonwoven material specimen and the hooks specimen must be mounted on the respective surfaces of the fixture such that shear force applied by the shear force weight is applied in the same direction as the shear force would be applied to the materials as they would be present as components of a fastening system on a wearable article in their intended use.

Remove the backing paper from the tape side of the prepared hooks material specimen and attach it, hooks down, to the downward-facing surface 52 on the upper fixture 50. The hooks material specimen should be oriented on the fixture relative the already-mounted nonwoven material specimen as the hooks material was oriented for use as a fastening component with the nonwoven material, on the article from which the samples were taken.

Program the tensile tester to move the upper fixture 50 down at 5 mm/sec for 49 mm, and then continue downward at 0.05 mm/sec until the target application force is detected at the load cell. Within 5 seconds of achieving the target application force, lower the movable platform 70 at a rate of 2.3 to 2.6 mm/sec to its lowest position. Within 5 seconds after the weight 68 is suspended, start data collection as the upper fixture is raised at 5.0 mm/sec until the hooks material specimen and nonwoven material specimen have become disengaged. The gage between the downward-facing surface 52 and the upward-facing surface 66 is set to 50 mm, and the movable platform 70 is at its highest vertical position for the start of the test. The test is run at each of the application force and shear force combinations set forth below.

Position the mounting plate 65/slide mechanism 64 such that the landing zone specimen is centered beneath the hook specimen. Using the linear actuator 69, set the movable platform 70 is to its highest vertical position with the selected shear force weight 68 resting on the platform. Zero the load cell and crosshead position, and start the test. Force (N) and vertical displacement (mm) data is collected. Peak Separation Resistance (N), Vertical Displacement at Peak Separation Resistance (mm), Separation Resistance at 0.5 mm vertical displacement (N) and Separation Resistance at 1.0 mm vertical displacement (N) are determined from the constructed Force (N) versus Vertical Displacement (mm) curve. Force measurements are recorded to the nearest 0.01 N and vertical displacements are recorded to the nearest 0.01 mm.

A total of six products (12 hook/loop pairs), are tested under the following application force and shear weight combinations.

1. 0.100 N application force with 100 g, 400 g, 700 g shear force weights
2. 0.550 N application force with 100 g, 400 g, 700 g shear force weights
3. 1.00 N application force with 100 g, 400 g, 700 g shear force weights Results (six left, six right) for each of the nine conditions are averaged separately and reported for Peak Separation Resistance (N), Separation Resistance at 0.5 mm vertical displacement (N) and Separation Resistance at 1.0 mm vertical displacement (N), each to the nearest 0.01 N, and Vertical Displacement at Peak Separation Resistance (mm) to the nearest 0.01 N.

Polymer Melting Point

Where a melting point for a polymer is discussed, specified or referred to herein, it is determined according to ISO 3146.

Polymer Density

Where a density of a polymer is discussed, specified or referred to herein, it is determined according to ISO 1183.

Polymer Melt Flow Rate

Where a melt flow rate of a polymer is discussed, specified or referred to herein, it is determined according to ISO 1133. Unless otherwise specified, analysis is performed at polymer temperature of 230° C. with a load of 2.160 kg.

Molecular Weight Polydispersity

Where a molecular weight polydispersity of a polymer is discussed, specified or referred to herein, it is determined according to ASTM D6474.

Polymer Viscosity Number

Where a viscosity number of a polymer is discussed, specified or referred to herein, it is determined according to ISO 307.

EXAMPLE

A bicomponent fiber nonwoven web was formed of spun bicomponent fibers having the following components and weight ratio:
  First polymer: MOPLEN HP462R polypropylene (a product of LyondellBasell, Rotterdam, Netherlands), 70% by weight
  Second polymer: ULTRAMID B27E polyamide (a product of BASF, Ludwigshafen, Germany), 30% by weight The fibers were spun in a side-by-side arrangement, to form bicomponent fibers of size 15-20 μm in diameter. The fibers were accumulated on a belt to form a batt of sufficient size to result in a bonded nonwoven web having a basis weight of 45 gsm. The batt was then consolidated by passage of the belt and the batt through the nip between a pair of compression rollers, and then thermally bonded between bonding rollers, to form a bonded multicomponent fiber nonwoven web. The bond pattern used was the "wavy" pattern as described herein, and particularly as appears in the landing zone material on current LUVS brand disposable diapers sold in the United States, manufactured by the Procter & Gamble Company, Cincinnati, Ohio. Following formation of the nonwoven web, the web was subjected to a flexographic printing process to imprint an aesthetic design thereon.

Samples of the Example nonwoven web were tested according to the Separation Resistance test set forth herein, with samples of Aplix "980" hooks as described herein.

Samples of a Prior Art bicomponent nonwoven web also were tested according to the Separation Resistance Test, with Aplix "980" hooks. The Prior Art material was manufactured by Mitsui Chemicals, Inc. (Tokyo, Japan), and was a 45 gsm nonwoven, having the same "wavy" bonding pattern as in the Example, formed of side-by-side bicomponent fibers having 20% by weight polypropylene component and 80% by weight polypropylene-polyethylene copolymer component. The Prior Art nonwoven web tested was the same or substantially similar to material present as landing zone material on current LUVS brand disposable diapers sold in the United States, manufactured by the Procter & Gamble Company, Cincinnati, Ohio, except that the Prior Art web tested had been further subjected to a flexographic printing process to imprint an aesthetic design thereon, similar to that of the Example.

The data obtained in the testing were as follows:

| Application Force (N) | Shear Force (N) | Material | Peak Separation Resistance (N) |
| --- | --- | --- | --- |
| 0.1 | 1.0 | Prior Art | 2.6 |
|  |  | Example | 3.7 |
|  | 4.0 | Prior Art | 4.6 |
|  |  | Example | 5.1 |
|  | 7.0 | Prior Art | 4.5 |
|  |  | Example | 5.7 |
| 0.55 | 1.0 | Prior Art | 3.6 |
|  |  | Example | 4.9 |
|  | 4.0 | Prior Art | 7.4 |
|  |  | Example | 9.4 |
|  | 7.0 | Prior Art | 9.0 |
|  |  | Example | 11 |
| 1.0 | 1.0 | Prior Art | 3.8 |
|  |  | Example | 5.1 |
|  | 4.0 | Prior Art | 8.9 |
|  |  | Example | 9.6 |
|  | 7.0 | Prior Art | 11 |
|  |  | Example | 12 |

The data set forth above show that the Example represents increased Separation Resistance performance over the Prior Art to which comparison was made. The data show that a multicomponent nonwoven web material having a basis weight less than 100 gsm, less than 75 gsm and less than 50 gsm may be made, and may be useful as the "loops" component of a hook-and-loop fastening system, which exhibits a Separation Resistance of: greater than 3.2 N at an application force of 0.1 N and a shear force of 1.0 N; greater than 4.9 N at an application force of 0.1 N and a shear force of 4.0 N; greater than 5.1 N at an application force of 0.1 N and a shear force of 7.0 N; greater than 4.3 N at an application force of 0.55 and a shear force of 1.0 N; greater than 8.4 N at an application force 0.55 N and a shear force of 4.0 N; greater than 10 N at an application force of 0.55 N and a shear force of 7.0 N; greater than 4.5 N at an application force of 1.0 N and a shear force of 1.0 N; greater than 9.3 N at an application force of 1.0 N and a shear force of 4.0 N; and greater than 11.5 N at an application force of 1.0 N and a shear force of 7.0 N. For improved separation resistance of a fastening system as contemplated herein, the lowest value of separation resistance for any combination of application force and shear force is at least 3.2 N, preferably greater than 3.5 and more preferably greater than 4.0.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples have been illustrated and described, it would be obvious to those skilled in the art that various other changes and modifications can be made without departing from the spirit and scope of the invention. It is therefore intended to cover in the appended claims all such changes and modifications that are contemplated.

What is claimed is:

1. A landing zone comprising a nonwoven web material operable to fastenably engage a fastening component, the nonwoven web material comprising multicomponent fibers, wherein:
   the multicomponent fibers have a polyolefin fiber component and a polyamide fiber component;
   the nonwoven web material has a machine direction, the multicomponent fibers have a machine direction bias, and the nonwoven web material bears an impressed pattern of thermal bonds; and
   the pattern of thermal bonds has an average frequency along any line that can be identified in the machine direction, of at least 0.5 bonds per cm.

2. The landing zone of claim 1, wherein the nonwoven web material comprises at least two layers of fibers including an underlying layer and an outward-facing layer comprising the multicomponent fibers.

3. The landing zone of claim 1, wherein the multicomponent fibers comprise from about 10% to about 50% by weight of the polyamide fiber component.

4. The landing zone of claim 1, wherein the polyamide fiber component is selected from the group consisting of polyamide 6, polyamide 6-6, a copolymer of polyamide 6 and polyamide 6-6, polyamide 6-10, polyamide 6-12, and combinations thereof.

5. The landing zone of claim 1, wherein the polyolefin is a polypropylene.

6. The landing zone of claim 1, wherein the melting temperatures of the polyolefin fiber component and the polyamide fiber component are within about 40° C. to about 120° C. of each other.

7. The landing zone of claim 1, wherein the respective densities of the polyolefin fiber component and the polyamide fiber component are within about 0.11 g/cm to about 0.45 g/cm of each other.

8. The landing zone of claim 2, wherein the underlying layer comprises monocomponent fibers formed of polyolefin.

9. The landing zone of claim 8, wherein the polyolefin comprises polypropylene.

10. A diaper comprising the landing zone of claim 1.

11. The landing zone of claim 1, wherein the pattern of thermal bonds comprises a first unit pattern and a second unit pattern, and wherein the first unit pattern is the same as the second unit pattern.

12. The landing zone of claim 1, wherein the pattern of thermal bonds comprises a unit pattern, wherein the unit pattern comprises a first segment having a first slope, wherein the unit pattern comprises a second segment having a second slope, and wherein the first slope is different than the second slope.

13. The landing zone of claim 1, wherein the pattern of thermal bonds comprises a unit pattern, wherein the unit pattern comprises a first segment having a positive slope, and wherein the unit pattern comprises a second segment having a negative slope.

14. A landing zone for an absorbent article comprising a nonwoven web material configured to receive a fastening component, the nonwoven web material comprising multicomponent fibers, wherein:
the multicomponent fibers have a polyolefin fiber component and a polyamide fiber component;
the nonwoven web material has a machine direction, the multicomponent fibers have a machine direction bias, and the nonwoven web material bears an impressed pattern of thermal bonds; and
the pattern of thermal bonds has an average frequency along any line that can be identified in the machine direction, of at least 0.5 bonds per cm.

15. The landing zone of claim 14, wherein the pattern of thermal bonds comprises a first unit pattern and a second unit pattern, and wherein the first unit pattern is the same as the second unit pattern.

16. The landing zone of claim 14, wherein the pattern of thermal bonds comprises a unit pattern, wherein the unit pattern comprises a first segment having a first slope, wherein the unit pattern comprises a second segment having a second slope, and wherein the first slope is different than the second slope.

17. The landing zone of claim 14, wherein the pattern of thermal bonds comprises a unit pattern, wherein the unit pattern comprises a first segment having a positive slope, and wherein the unit pattern comprises a second segment having a negative slope.

18. The landing zone of claim 17, wherein an acute angle is formed into the pattern of thermal bonds between the first segment and the second segment.

19. A outer layer component of a multilayer backsheet for an absorbent article, the outer layer component comprising a landing zone, the landing zone comprising a nonwoven web material configured to receive a fastening component, the nonwoven web material comprising multicomponent fibers, wherein:
the multicomponent fibers have a polyolefin fiber component and a polyamide fiber component;
the nonwoven web material has a machine direction, the multicomponent fibers have a machine direction bias, and the nonwoven web material bears an impressed pattern of thermal bonds; and
the pattern of thermal bonds has an average frequency along any line that can be identified in the machine direction, of at least 0.5 bonds per cm.

20. The landing zone of claim 19, wherein the pattern of thermal bonds comprises a unit pattern, wherein the unit pattern comprises a first segment having a positive slope, and wherein the unit pattern comprises a second segment having a negative slope.

* * * * *